US011833222B2

(12) United States Patent
Gomez De La Cuesta et al.

(10) Patent No.: US 11,833,222 B2
(45) Date of Patent: *Dec. 5, 2023

(54) CL AND/OR CH1 MUTATED ANTIBODIES FOR DRUG CONJUGATION

(71) Applicant: LONZA LTD, Visp (CH)

(72) Inventors: Ramon Gomez De La Cuesta, Hertfordshire (GB); Jesús Zurdo, Cambridgeshire (GB); Lars Arne Andreas Arnell, Suffolk (GB); Laurent Ducry, Sierre (CH); Laurence Bonnafoux, Martigny (CH)

(73) Assignee: LONZA LTD, Visp (CH)

( * ) Notice: Subject to any disclaimer, the term of this patent is extended or adjusted under 35 U.S.C. 154(b) by 577 days.

This patent is subject to a terminal disclaimer.

(21) Appl. No.: 17/019,537

(22) Filed: Sep. 14, 2020

(65) Prior Publication Data

US 2021/0100914 A1    Apr. 8, 2021

Related U.S. Application Data

(63) Continuation of application No. 15/550,903, filed as application No. PCT/EP2016/053162 on Feb. 15, 2016, now Pat. No. 10,953,106.

(30) Foreign Application Priority Data

Feb. 16, 2015  (GB) ..................................... 1502591
Mar. 23, 2015  (GB) ..................................... 1504858

(51) Int. Cl.
  *A61K 47/68*   (2017.01)
  *C07K 16/00*   (2006.01)
  *A61P 35/00*   (2006.01)
  *C07K 16/30*   (2006.01)

(52) U.S. Cl.
  CPC ...... *A61K 47/6855* (2017.08); *A61K 47/6803* (2017.08); *A61P 35/00* (2018.01); *C07K 16/00* (2013.01); *C07K 16/3015* (2013.01); *C07K 2317/32* (2013.01); *C07K 2317/515* (2013.01); *C07K 2317/522* (2013.01); *C07K 2317/73* (2013.01); *C07K 2319/01* (2013.01)

(58) Field of Classification Search
  CPC ............ A61K 47/6855; A61K 47/6803; A61P 35/00; C07K 16/00; C07K 16/3015; C07K 2317/32; C07K 2317/515; C07K 2317/522; C07K 2317/73; C07K 2319/01
  See application file for complete search history.

(56) References Cited

U.S. PATENT DOCUMENTS

| 7,723,485 | B2 | 5/2010 | Junutula et al. |
| 9,150,639 | B2 | 10/2015 | Yamasaki et al. |
| 2007/0092940 | A1 | 4/2007 | Eigenbrot et al. |
| 2009/0010945 | A1 | 1/2009 | Alley et al. |
| 2009/0258420 | A1 | 10/2009 | van Vlijmen et al. |
| 2009/0280056 | A1 | 11/2009 | Dennis et al. |
| 2013/0230886 | A1 | 9/2013 | Voltsmeier et al. |
| 2014/0112914 | A1 | 4/2014 | Nezu et al. |
| 2014/0323315 | A1* | 10/2014 | Bobrowicz ............ G01N 33/68 506/14 |
| 2014/0370020 | A1 | 12/2014 | Kuramochi et al. |
| 2016/0008485 | A1 | 1/2016 | Marquette et al. |
| 2016/0051695 | A1* | 2/2016 | Lin .................... A61K 47/6889 424/179.1 |

FOREIGN PATENT DOCUMENTS

| CN | 104011207 B | 9/2018 |
| JE | 2008516896 A | 5/2008 |
| JP | 2010526821 A | 8/2010 |
| JP | 2011509675 A | 3/2011 |
| JP | 2015502397 A | 1/2015 |
| JP | 2016528882 B2 | 9/2016 |
| JP | 2017525755 A | 9/2017 |
| WO | 2009092011 A1 | 7/2009 |
| WO | 2011118739 A1 | 9/2011 |
| WO | 2012073985 A1 | 6/2012 |
| WO | 2013065708 A1 | 5/2013 |
| WO | 2013093809 A1 | 6/2013 |
| WO | 2013109994 A1 | 7/2013 |
| WO | 2013185115 A1 | 12/2013 |
| WO | 2014072888 A1 | 5/2014 |
| WO | 2014081955 A1 | 5/2014 |

(Continued)

OTHER PUBLICATIONS

Panowski et al. (mAbs, 6(1): 34-45, 2014).*
Axup et al., "Synthesis of site-specific antibody-drug conjugates using unnatural amino acids," PNAS, vol. 109, No. 40, 16101-16106 (2012).
Bhat et al., The Next Step in Homogenous Bioconjugate Development: Optimizing Payload Placemen and Conjugate Composition, BioProcess International: 12(9)s: 10-25 (2014).
Great Britain Search Report for Application No. GB1502591.9, dated Nov. 12, 2015.
International Search Report for International Patent Application No. PCT/EP2016/053162; dated Oct. 27, 2016.
Junutula et al., Site-specific conjugation of a cytotoxic drug to an antibody improves the therapeutic index, Nature Biotechnology, 26(8): 925-932 (2008).

(Continued)

*Primary Examiner* — Nelson B Moseley, II
(74) *Attorney, Agent, or Firm* — MEDLER FERRO WOODHOUSE & MILLS PLLC

(57) ABSTRACT

Antibodies having modified constant regions so as to permit conjugation of the antibody to a payload such as a therapeutic agent are described. Preferred antibodies include a mutation at light chain position 180 (positional numbering), most preferably the mutation is to a residue selected from C, K, Q, or a non-natural amino acid. Additional mutations may also be combined with a mutation at position 180; including one or more of light chain (LC) S208, LC S171, LC S182, LC A184, LC V191, LC S202, LC S203, LC T206, heavy chain (HC) S160, HC T190, HC S443, HC S447, HC S139, HC S168, HC V170, HC V176, HC T200, HC S445 according to a positional numbering convention.

17 Claims, 6 Drawing Sheets

Specification includes a Sequence Listing.

(56) References Cited

FOREIGN PATENT DOCUMENTS

| WO | 2014124316 A2 | 8/2014 |
| WO | 2014177771 A1 | 11/2014 |
| WO | 2014210064 A1 | 12/2014 |
| WO | 2015195904 A1 | 12/2015 |
| WO | 2016040856 A2 | 3/2016 |

OTHER PUBLICATIONS

Junutula et al., "Rapid identification of reactive cysteine residues for site-specific labeling of antibody-Fabs," Journal of mmunological Methods, 332:41-52 (2008).

Junutula et al., "Engineered thio-Trastuzumab-DM1 Conjugate with an Improved Therapeutic Index to Target Human Epidermal Growth Factor Receptor 2-Positive Breast Cancer," Clinical Cancer Research, www.aacrjournals.org, 4769—Aug. 30, 2010.

Panowski et al., Site-specific antibody drug conjugates for cancer therapy, Landes Bioscience, 6(1): 24-45 (2014).

Pillow et al., "Site-Specific Trastuzumab Maytansinoid Antibody-Drug conjugates with Improved Therapeutic Activity Through Linker and Antibody Engineering," Journal of Medicinal Chemistry, 57:7890-7899 (2014).

Voynov et al., "Design and application of antibody cysteine variants," Bioconjug Chem. 17;21(220):385-92 (2010).

* cited by examiner

|  | % Monomer | % Monomer after conj. | % aggregation | % fragmentation |
|---|---|---|---|---|
| Herceptin | 94.46 | 78.53 | 3.34 | 18.09 |
| LCHerS208C | 95.28 | 54.06 | 1.36 | 44.56 |
| HCHerS443C | 94.20 | 60.83 | 8.05 | 31.00 |
| LCHerS202C | 94.90 | 69.00 | 2.70 | 28.22 |
| HCHerT200C | 96.26 | 94.94 | 2.12 | 2.91 |
| HCHerV170C | 96.06 | 93.54 | 1.28 | 3.87 |
| HCHerS447C | 90.41 | 66.94 | 8.03 | 25.01 |
| LCHerV191C | 95.67 | 95.73 | 2.41 | 1.84 |
| HCHerS445C | 98.59 | 77.22 | 0.65 | 22.11 |
| HCHerS168C | 95.13 | 78.01 | 2.29 | 19.68 |
| HCHerT190C | 98.01 | 77.19 | 2.60 | 20.17 |
| HCHerS139C | 95.25 | 80.27 | 2.42 | 17.29 |
| LCHerT206C | 95.04 | 82.70 | 1.67 | 16.01 |
| LCHerT180C | 96.27 | 84.58 | 1.77 | 13.64 |
| HCHerS160C | 95.52 | 81.03 | 1.61 | 17.29 |
| LCHerS182C | 87.13 | 73.15 | 8.51 | 18.32 |
| LCHerA184C | 87.44 | 80.20 | 2.14 | 17.65 |
| LCHerS203C | 83.61 | 58.22 | 2.01 | 39.76 | ns

SEQUENCE LISTING

<160> NUMBER OF SEQ ID NOS: 40

<210> SEQ ID NO 1
<211> LENGTH: 214
<212> TYPE: PRT
<213> ORGANISM: Artificial Sequence
<220> FEATURE:
<223> OTHER INFORMATION: trastuzumab unmodified light chain

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 2
<211> LENGTH: 448
<212> TYPE: PRT
<213> ORGANISM: Artificial Sequence
<220> FEATURE:
<223> OTHER INFORMATION: trastuzumab unmodified heavy chain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
        100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 3
<211> LENGTH: 450
<212> TYPE: PRT
<213> ORGANISM: Artificial Sequence
<220> FEATURE:
<223> OTHER INFORMATION: modified heavy chain

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Cys Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 4
<211> LENGTH: 450
<212> TYPE: PRT
<213> ORGANISM: Artificial Sequence
<220> FEATURE:
<223> OTHER INFORMATION: modified heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Cys
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 5
<211> LENGTH: 450
<212> TYPE: PRT
<213> ORGANISM: Artificial Sequence
<220> FEATURE:
<223> OTHER INFORMATION: modified heavy chain

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Cys Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 6
<211> LENGTH: 450
<212> TYPE: PRT
<213> ORGANISM: Artificial Sequence
<220> FEATURE:
<223> OTHER INFORMATION: modified heavy chain

<400> SEQUENCE: 6

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Cys His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 7
<211> LENGTH: 450
<212> TYPE: PRT
<213> ORGANISM: Artificial Sequence
<220> FEATURE:
<223> OTHER INFORMATION: modified heavy chain

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Cys
            165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205
```

```
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
        260                 265                 270
Asp Pro Glu Val Lys Phe Asn Trp Tyr Val Asp Gly Val Glu Val His
    275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Glu Glu Met Thr Lys Asn Gln Val Ser Leu
    355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys
    450

<210> SEQ ID NO 8
<211> LENGTH: 450
<212> TYPE: PRT
<213> ORGANISM: Artificial Sequence
<220> FEATURE:
<223> OTHER INFORMATION: modifed heavy chain

<400> SEQUENCE: 8

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
            85                  90                  95
Ser Arg Trp Gly Gly Asp Gly Phe Tyr Ala Met Asp Tyr Trp Gly Gln
        100                 105                 110
```

```
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Cys Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 9
<211> LENGTH: 450
<212> TYPE: PRT
<213> ORGANISM: Artificial Sequence
<220> FEATURE:
<223> OTHER INFORMATION: modifed heavy chain

<400> SEQUENCE: 9

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Lys Asp Thr
         20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Cys Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

-continued

Glu Ala Leu His Asn His Tyr Thr Gln Lys Ser Leu Ser Leu Ser Pro
            435                 440                 445

Gly Lys
    450

<210> SEQ ID NO 10
<211> LENGTH: 450
<212> TYPE: PRT
<213> ORGANISM: Artificial Sequence
<220> FEATURE:
<223> OTHER INFORMATION: modifed heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Cys Leu Ser Leu Ser Pro
        435                 440                 445

Gly Lys
    450

<210> SEQ ID NO 11
<211> LENGTH: 450
<212> TYPE: PRT
<213> ORGANISM: Artificial Sequence
<220> FEATURE:
<223> OTHER INFORMATION: modifed heavy chain

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Cys Leu Ser Pro
        435                 440                 445

Gly Lys
    450

<210> SEQ ID NO 12
<211> LENGTH: 450
<212> TYPE: PRT
<213> ORGANISM: Artificial Sequence
<220> FEATURE:
<223> OTHER INFORMATION: modified heavy chain

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Cys Pro
    435                 440                 445

Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: modifed light chain

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Cys Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
210

<210> SEQ ID NO 14
<211> LENGTH: 214
<212> TYPE: PRT
<213> ORGANISM: Artificial Sequence
<220> FEATURE:
<223> OTHER INFORMATION: modified light chain

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Cys Leu Ser Lys Ala Asp Tyr Glu Lys His Lys Val Tyr
                180                 185                 190
```

```
Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 15
<211> LENGTH: 214
<212> TYPE: PRT
<213> ORGANISM: Artificial Sequence
<220> FEATURE:
<223> OTHER INFORMATION: modified light chain

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 16
<211> LENGTH: 214
<212> TYPE: PRT
<213> ORGANISM: Artificial Sequence
<220> FEATURE:
<223> OTHER INFORMATION: modified light chain

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

-continued

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Cys Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 17
<211> LENGTH: 214
<212> TYPE: PRT
<213> ORGANISM: Artificial Sequence
<220> FEATURE:
<223> OTHER INFORMATION: modified light chain

<400> SEQUENCE: 17

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Cys Tyr
            180                 185                 190

Ala Cys Glu Val Thr His Gln Gly Leu Ser Ser Pro Val Thr Lys Ser
        195                 200                 205
```

```
<210> SEQ ID NO 18
<211> LENGTH: 214
<212> TYPE: PRT
<213> ORGANISM: Artificial Sequence
<220> FEATURE:
<223> OTHER INFORMATION: modified light chain

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Cys Ser Pro Val Thr Lys Ser
        195                 200                 205

Phe Asn Arg Gly Glu Cys
    210

<210> SEQ ID NO 19
<211> LENGTH: 214
<212> TYPE: PRT
<213> ORGANISM: Artificial Sequence
<220> FEATURE:
<223> OTHER INFORMATION: modified light chain

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60
```

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Cys Pro Val Thr Lys Ser
            195                 200                 205

Phe Asn Arg Gly Glu Cys
    210

<210> SEQ ID NO 20
<211> LENGTH: 214
<212> TYPE: PRT
<213> ORGANISM: Artificial Sequence
<220> FEATURE:
<223> OTHER INFORMATION: modified light chain

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Cys Lys Ser
            195                 200                 205

```
Phe Asn Arg Gly Glu Cys
    210

<210> SEQ ID NO 21
<211> LENGTH: 214
<212> TYPE: PRT
<213> ORGANISM: Artificial Sequence
<220> FEATURE:
<223> OTHER INFORMATION: modified light chain

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Cys
        195                 200                 205

Phe Asn Arg Gly Glu Cys
    210

<210> SEQ ID NO 22
<211> LENGTH: 23
<212> TYPE: PRT
<213> ORGANISM: Artificial Sequence
<220> FEATURE:
<223> OTHER INFORMATION: heavy chain mutation
<220> FEATURE:
<221> NAME/KEY: Mutagen
<222> LOCATION: (11)..(11)
<223> OTHER INFORMATION: Cteine, Kine, Etamine or non-natural amino acid

<400> SEQUENCE: 22

Phe Pro Leu Ala Pro Ser Ser Lys Ser Thr Xaa Ala Ala Gly Gly Thr
1               5                   10                  15

Ala Ala Leu Gly Cys Leu Val
            20

<210> SEQ ID NO 23
<211> LENGTH: 23
```

```
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 23

Lys Asp Tyr Phe Pro Glu Pro Val Thr Val Xaa Ala Ala Trp Asn Ser
1               5                   10                  15

Gly Ala Leu Thr Ser Gly Val
            20

<210> SEQ ID NO 24
<211> LENGTH: 23
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 24

Thr Val Ser Trp Asn Ser Gly Ala Leu Thr Xaa Ala Ala Gly Val His
1               5                   10                  15

Thr Phe Pro Ala Val Leu Gln
            20

<210> SEQ ID NO 25
<211> LENGTH: 23
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 25

Ser Trp Asn Ser Gly Ala Leu Thr Ser Gly Xaa Ala Ala His Thr Phe
1               5                   10                  15

Pro Ala Val Leu Gln Ser Ser
            20

<210> SEQ ID NO 26
<211> LENGTH: 23
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 26

Leu Thr Ser Gly Val His Thr Phe Pro Ala Xaa Ala Ala Leu Gln Ser
1               5                   10                  15

Ser Gly Leu Tyr Ser Leu Ser
            20

<210> SEQ ID NO 27
```

```
<211> LENGTH: 23
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 27

Ser Gly Leu Tyr Ser Leu Ser Ser Val Val Xaa Ala Ala Val Pro Ser
1               5                   10                  15

Ser Ser Leu Gly Thr Gln Thr
            20

<210> SEQ ID NO 28
<211> LENGTH: 23
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 28

Thr Val Pro Ser Ser Ser Leu Gly Thr Gln Xaa Ala Ala Tyr Ile Cys
1               5                   10                  15

Asn Val Asn His Lys Pro Ser
            20

<210> SEQ ID NO 29
<211> LENGTH: 20
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 29

Glu Ala Leu His Asn His Tyr Thr Gln Lys Xaa Ala Ala Leu Ser Leu
1               5                   10                  15

Ser Pro Gly Lys
            20

<210> SEQ ID NO 30
<211> LENGTH: 20
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 30

Glu Ala Leu His Asn His Tyr Thr Gln Lys Xaa Ala Ala Leu Ser Leu
1               5                   10                  15

Ser Pro Gly Lys
            20
```

```
<210> SEQ ID NO 31
<211> LENGTH: 20
<212> TYPE: PRT
<213> ORGANISM: Artificial Sequence
<220> FEATURE:
<223> OTHER INFORMATION: heavy chain mutation
<220> FEATURE:
<221> NAME/KEY: MUTAGEN
<222> LOCATION: (15)..(15)
<223> OTHER INFORMATION: Cteine, Kine, Etamine or non-natural amino acid

<400> SEQUENCE: 31

Glu Ala Leu His Asn His Tyr Thr Gln Lys Ser Leu Ser Leu Xaa Ala
1               5                   10                  15

Ala Pro Gly Lys
            20

<210> SEQ ID NO 32
<211> LENGTH: 23
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 32

Glu Ser Val Thr Glu Gln Asp Ser Lys Asp Xaa Ala Ala Thr Tyr Ser
1               5                   10                  15

Leu Ser Ser Thr Leu Thr Leu
            20

<210> SEQ ID NO 33
<211> LENGTH: 23
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 33

Asp Ser Thr Tyr Ser Leu Ser Ser Thr Leu Xaa Ala Ala Leu Ser Lys
1               5                   10                  15

Ala Asp Tyr Glu Lys His Lys
            20

<210> SEQ ID NO 34
<211> LENGTH: 23
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 34

Thr Tyr Ser Leu Ser Ser Thr Leu Thr Leu Xaa Ala Ala Lys Ala Asp
1               5                   10                  15

Tyr Glu Lys His Lys Val Tyr
            20
```

```
<210> SEQ ID NO 35
<211> LENGTH: 23
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 35

Ser Leu Ser Ser Thr Leu Thr Leu Ser Lys Xaa Ala Ala Asp Tyr Glu
1               5                   10                  15

Lys His Lys Val Tyr Ala Cys
            20

<210> SEQ ID NO 36
<211> LENGTH: 23
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 36

Leu Ser Lys Ala Asp Tyr Glu Lys His Lys Xaa Ala Ala Tyr Ala Cys
1               5                   10                  15

Glu Val Thr His Gln Gly Leu
            20

<210> SEQ ID NO 37
<211> LENGTH: 23
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 37

Tyr Ala Cys Glu Val Thr His Gln Gly Leu Xaa Ala Ala Ser Pro Val
1               5                   10                  15

Thr Lys Ser Phe Asn Arg Gly
            20

<210> SEQ ID NO 38
<211> LENGTH: 23
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 38

Ala Cys Glu Val Thr His Gln Gly Leu Ser Xaa Ala Ala Pro Val Thr
1               5                   10                  15

Lys Ser Phe Asn Arg Gly Glu
            20
```

```
<210> SEQ ID NO 39
<211> LENGTH: 21
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (11)..(11)
<223> OTHER INFORMATION: Cteine, Kine, Etamine or non-natural amino acid

<400> SEQUENCE: 39

Val Thr His Gln Gly Leu Ser Ser Pro Val Xaa Ala Ala Lys Ser Phe
1               5                   10                  15

Asn Arg Gly Glu Cys
            20

<210> SEQ ID NO 40
<211> LENGTH: 21
<212> TYPE: PRT
<213> ORGANISM: Artificial Sequence
<220> FEATURE:
<223> OTHER INFORMATION: light chain mutation
<220> FEATURE:
<221> NAME/KEY: MUTAGEN
<222> LOCATION: (13)..(13)
<223> OTHER INFORMATION: Cteine, Kine, Etamine or non-natural amino acid

<400> SEQUENCE: 40

Val Thr His Gln Gly Leu Ser Ser Pro Val Thr Lys Xaa Ala Ala Phe
1               5                   10                  15

Asn Arg Gly Glu Cys
            20
```

CL AND/OR CH1 MUTATED ANTIBODIES FOR DRUG CONJUGATION

SEQUENCE LISTING

The instant application contains a Sequence Listing which was submitted electronically in ASCII format on Jun. 24, 2023 and is hereby incorporated by reference in its entirety. Said ASCII copy, created on Jun. 17, 2023, is named 0132-0123US2_ST25.txt and is 70,693 bytes in size.

FIELD OF THE INVENTION

The present invention relates to antibodies which include a modified constant region so as to permit conjugation of the antibody to a payload such as a radionuclide, a polymer, a cytotoxic agent or a drug moiety. Preferably the conjugated antibodies yield a desired payload to antibody ratio. Aspects of the invention relate to payload-antibody conjugates.

BACKGROUND TO THE INVENTION

Antibody-drug conjugates (ADCs) are a class of targeted therapies which combine the specificity of antibodies with the cytotoxicity of cytotoxic therapeutics. ADCs are primarily considered candidates for the treatment of various cancers. ADCs comprise an antibody linked to a therapeutic drug.

One problem with development of ADCs is the conjugation technology used; if drugs are conjugated non-selectively to cysteine or lysine residues in the antibody, then this can result in a heterogeneous mixture of ADCs. This approach leads to suboptimal safety and efficacy properties and makes optimization of the biological, physical and pharmacological properties of an ADC challenging. In particular, heterogeneity can be a problem with respect to the distribution of cytotoxins (that is, site of attachment), and the loading of cytotoxins (that is, number of drug molecules per antibody).

Heterogeneity presents safety concerns since high drug/antibody ratio (DAR) species can have poor binding to their target and increase risks of off-target toxicity. Low drug loading species are less active (DAR 1) or inactive (DAR 0). As the number of drugs per mAb decreases, the pharmacokinetic properties of the ADC improves (Hamblett, Clin. Cancer Res. 2004, 10, 7063-7070). Furthermore, heterogeneity of ADCs leads to challenges associated with consistent manufacturing and analytical testing.

Site-selective conjugation (SSC) would presumably improve ADCs' safety and efficacy, and thus, results in higher ADC quality. Junutula et al Nature Biotech 2008 report that same activity is achieved with half ADC dose in a SSC-ADC compared to control. Thus, ADC homogeneity will improve Therapeutic Index (TI is the ratio between maximum tolerated dose and effective dose. (TI=TD50/ED50)). Furthermore, higher DAR homogeneity would result in:
  Simpler product characterization for regulatory filings, better defined product specifications and
  Reduced off-target or bystander toxicity
  Potentially more controlled pharmacology (fewer species to reckon on)
  Potentially reduce dosage requirements (per gram) to achieve similar pharmacological effect—Reduced potential incidence of side-effects (e.g. immunogenicity, toxicity, etc.)
  Reduced costs due to higher conjugation yields and reduced dosage (required amount of ADC to be administered)

However, simply making antibodies with modified residues may result in unforeseen effects, such as changes to antibody aggregation propensity, solubility, or efficacy. The present applicants therefore developed a rational screening process to determine which residues may be modified. In selected embodiments, the modification achieves an antibody suitable for conjugation to a payload (such as a drug) to give a DAR of around 2.

SUMMARY OF THE INVENTION

According to a first aspect of the invention, there is provided an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the one or more mutations include a mutation at light chain position 180 (positional numbering).

The antibody may comprise two introduced site specific conjugation sites.

In preferred embodiments, the wild type residue at position 180 is T. The mutated residue at position 180 is preferably selected from cysteine, lysine, glutamine, or a non-natural amino acid, and is most preferably cysteine.

In certain embodiments, the antibody may further comprise one or more mutations selected from light chain (LC) S208, LC S171, LC S182, LC A184, LC V191, LC S202, LC S203, LC T206, heavy chain (HC) S160, HC T190, HC S443, HC S447, HC S139, HC S168, HC V170, HC V176, HC T200, HC S445 according to a positional numbering convention. Preferred mutations are at one or more positions selected from residues 206 (light chain), 160, 190, 443, and 447 (heavy chain) (positional numbering). The mutated residues are preferably independently selected from cysteine, lysine, glutamine, or a non-natural amino acid, and is most preferably cysteine. For example, the modification of antibodies with non-natural amino acids is described in WO2013/185115.

According to a further aspect of the invention, there is provided an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the antibody comprises the amino acid sequence of SEQ ID No 33; where X is selected from C, K, Q, or a non-natural amino acid. The antibody may further comprise one or more amino acid sequences selected from the group consisting of SEQ ID No 22-32 and SEQ ID No 34-40; where each X is independently selected from C, K, Q, or a non-natural amino acid, and is most preferably cysteine.

According to a second aspect of the invention, there is provided an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the one or more mutations include a mutation at light chain position 208 (positional numbering).

The antibody may comprise two introduced site specific conjugation sites.

In preferred embodiments, the wild type residue at position 208 is S. The mutated residue at position 208 is preferably selected from cysteine, lysine, glutamine, or a non-natural amino acid, and is most preferably cysteine.

In certain embodiments, the antibody may further comprise one or more mutations selected from light chain (LC) T180, LC S171, LC S182, LC A184, LC V191, LC S202, LC S203, LC T206, heavy chain (HC) S160, HC T190, HC S443, HC S447, HC S139, HC S168, HC V170, HC V176, HC T200, HC S445 according to a positional numbering convention. Preferred mutations are at one or more positions selected from residues 180, 206 (light chain), 160, 190, 443, and 447 (heavy chain) (positional numbering). The mutated residues are preferably independently selected from cysteine, lysine, glutamine, or a non-natural amino acid, and is most preferably cysteine. For example, the modification of antibodies with non-natural amino acids is described in WO2013/185115.

According to a further aspect of the invention, there is provided an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the antibody comprises the amino acid sequence of SEQ ID No 40; where X is selected from C, K, Q, or a non-natural amino acid. The antibody may further comprise one or more amino acid sequences selected from the group consisting of SEQ ID No 22-39; where each X is independently selected from C, K, Q, or a non-natural amino acid, and is most preferably cysteine.

The invention further provides an isolated or engineered antibody, or a fragment or derivative thereof, having a variable region which binds a target molecule, and a constant region, wherein the constant region comprises one or more mutations introducing a site specific conjugation site by:
  a) substituting a residue selected from the group consisting of light chain (LC) T180, LC S208, LC S171, LC S182, LC A184, LC V191, LC S202, LC S203, LC T206, heavy chain (HC) S160, HC T190, HC S443, HC S447, HC S139, HC S168, HC V170, HC V176, HC T200, HC S445 according to a positional numbering convention with a cysteine residue, a lysine residue, a glutamine residue or a non-natural amino acid; or
  b) introducing a cysteine substitution at a residue selected from the group consisting of LC T180C, LC S208C, LC S171C, LC S182C, LC A184C, LC V191C, LC S202C, LC S203C, LC T206C, HC S160C, HC T190C, HC S443C, HC S447C, HC S139C, HC S168C, HC V170C, HC V176C, HC T200C, HC S445C according to a positional numbering convention; or
  c) comprising at least one amino acid sequence selected from the group consisting of: SEQ ID No 22 to 40, wherein X is a cysteine residue, a lysine residue, a glutamine residue or a non-natural amino acid; or
  d) comprising at least one amino acid sequence selected from the group consisting of: SEQ ID No 22 to 40, wherein X is a cysteine residue.

The invention still further provides an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the antibody includes a light chain constant region comprising the amino acid sequence of residues 109-214 of SEQ ID No 14.

The invention also provides an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the antibody includes a light chain constant region comprising the amino acid sequence of residues 109-214 of SEQ ID No 21.

The following features may apply to all aspects of the invention. The antibody is preferably selected from the group comprising IgG1, IgG2, IgG3, and IgG4. The light chain may either be kappa or lambda light chain, the light chain constant region either C kappa (Ck) or C lambda (Cλ). The constant region may comprise at least a portion of an IgG1 constant region, preferably one or more, preferably all, of the Ck, CH1 and CH3 domains of the IgG1 constant region. The antibody may be selected from the group consisting of Fabs, bi specific antibody fragments (tandem scFv-Fc, scFv-Fc knobs-into-holes, scFv-Fc-scFv, F(ab')2, Fab-scFv, (Fab'scFv)2, scDiabody-Fc, or scDiabody-CH3), IgG-based bispecific antibodies (Hybrid hybridoma, Knobs-into-holes with common light chain, Two-in-one IgG, Dual V domain IgG, IgG-scFv, scFv-IgG, IgG-V, V-IgG), minibody, tribi-minibody, nanobodies, and di-diabody. The antibody may be human, humanised, or chimeric.

Preferred antibodies are selected from Abciximab; Rituximab; Basiliximab; Daclizumab; Palivizumab; Infliximab; Trastuzumab; Alemtuzumab; Adalimumab; Efalizumab; Cetuximab; Ibritumomab; Omalizumab; Bevacizumab; Ranibizumab; Golimumab; Canakinumab; Ustekinumab; Tocilizumab; Ofatumumab; Belimumab; Ipilimumab; Brentuximab; Pertuzumab; Raxibacumab; Vedolizumab; Ramucirumab; Obinutuzumab; Siltuximab; Secukinumab; Dinutuximab.

The antibody may lack one or more Fc effector functions; may lack ADCC activity; or may have increased ADCC activity.

A further aspect of the invention provides an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the antibody includes a light chain comprising the amino acid sequence of SEQ ID No 14. The antibody may include a heavy chain comprising an amino acid sequence selected from SEQ ID No 2 to SEQ ID No 12.

In another aspect of the invention provides an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the antibody includes a light chain comprising the amino acid sequence of SEQ ID No 21. The antibody may include a heavy chain comprising an amino acid sequence selected from SEQ ID No 2 to SEQ ID No 12.

The invention further provides an immunoconjugate comprising an antibody according to any of the preceding aspects of the invention, a payload, and a linker joining the payload to the antibody. The linker may be selected from 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1 carboxylate (SMCC), N-Succinimidyl, (4-iodo-acetyl) aminobenzoate (SIAB), and 6-maleimidocaproyl-valine-citrulline-p-aminobenyloxycarbonyl (MC-vc-PAB); or is a branched linker which comprises a peptide chain and is derived from o-hydroxy p-amino benzylic alcohol, wherein the peptide chain is connected to the phenyl ring via the p-amino group, the payload is connected to the phenyl ring via the benzylic alcohol moiety, and the antibody is connected to the phenyl ring via the o-hydroxy group.

The payload may be selected from the group consisting of a radionuclide, a chemotherapeutic agent, a cytotoxic agent, a microbial toxin, a plant toxin, a polymer, a carbohydrate, a cytokine, a fluorescent label, a luminescent label, an enzyme-substrate label, an enzyme, a peptide, a peptidomimetic, a nucleotide, an siRNA, a microRNA, an RNA mimetic, and an aptamer. A preferred polymer is a PEG molecule. Other preferred payloads include 90Y, 131I, 67Cu, 177Lu, 213Bi, 211At, dolastatin, vedotin, monomethyl auristatin F, maytansinoids including DM1 and DM4, duocarmycin analogs, calicheamicin, pyrrolobenzodiazepines, centanamycin, irinotecan, and doxorubicin, *Pseudomonas* exotoxin A, Diphtheria toxin, ricin, polyethylene glycol, hydroxyethyl starch, and a mannosyl residue. The payload may be a microtubule disrupting agent, or a DNA modifying agent.

The invention further provides a pharmaceutical composition comprising an antibody or an immunoconjugate according to any of the above aspects, and a pharmaceutically acceptable diluent, carrier or excipient.

Also provided is a method for generating an immunoconjugate, the method comprising conjugating an antibody according to any of the above aspects to a payload.

A process for preparing an antibody may comprise:
(i) mutagenizing a nucleic acid sequence of a parent antibody by replacing one or more amino acid residues with a mutant residue to encode the antibody;
(ii) expressing the mutant antibody; and
(iii) isolating the mutant antibody.

The antibody may be expressed in a prokaryotic (such as *E. coli* or *Bacillus*) or an eukaryotic cell (such as yeast (Pichia, Saccharomyces, Hansenula, Yarrowia) or mammalian cells (CHO cells, NSO cells, SP2/0 cells, 293 cells) or insect cells (SF9 cells).

The process may further comprise:
(i) reacting the mutant antibody with a thiol-reactive affinity reagent to generate an affinity labelled, antibody; and
(ii) measuring the binding of the affinity labelled antibody to a capture media.

Other aspects of the invention provide an antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, such that from 85% to 110% of site specific conjugation sites per antibody are conjugated to a payload. In a preferred embodiment at least 90%, at least 95%, or at least 100% of site specific conjugation sites per antibody are conjugated to a payload. In a preferred embodiment, the antibody comprises two site specific conjugation sites (ie, one on either the heavy or light chain, and two such chains per antibody). For such an antibody, 85-110% conjugation yields a drug-antibody ratio (DAR) of from 1.7-2.2. In certain embodiments, the DAR is preferably from 1.8-2.1, more preferably from 1.9-2.1, and most preferably around 2.0.

In another preferred embodiment, the antibody comprises four site specific conjugation sites (ie, one on the heavy and one on the light chain, or two on the heavy and none on the light chain, or none on the heavy and two on the light chain, and two such chains per antibody). For such an antibody, 85-110% conjugation yields a drug-antibody ratio (DAR) of from 2×(1.7-2.2) i.e. 3.4-4.4. In certain embodiments, the DAR is preferably from 2×1.8-2.1, i.e. 3.6-4.2, more preferably from 2×1.9-2.1 i.e. 3.8-4.2, and most preferably around 2×2.0 i.e. 4.

The antibody, fragment, or derivative may be conjugated directly or indirectly to the payload; indirect conjugation may take place via a linker. The antibody may further comprise a linker. Suitable linkers include maleimide linkers, which permit conjugation to a payload via succinimide conjugation. The linker may be cleavable, or non-cleavable. Other suitable linkers are disclosed in international patent application WO2012/113847, which describes a branched linker which comprises a peptide chain and is derived from o-hydroxy p-amino benzylic alcohol, wherein the peptide chain is connected to the phenyl ring via the p-amino group, the drug is connected to the phenyl ring via the benzylic alcohol moiety, and the antibody is connected to the phenyl ring via the o-hydroxy group.

The constant region preferably comprises at least a portion of an IgG IgA, IgD, IgE, or IgM constant region, more preferably a human IgG constant region. In preferred embodiments, the constant region is a full length IgG constant region, although in other embodiments truncated constant regions or light or heavy chain only constant regions may be used. For example, the constant region may comprise one or more, preferably all, of the Ck, CH1 and CH3 domains of the IgG constant region. A preferred IgG is IgG1, other IgG include IgG2, IgG3, and IgG4.

By "antibody" is meant any antigen-binding immunoglobulin molecule. The antibody is preferably a complete mammalian antibody (comprising two heavy chains and two light chains, each of which includes a constant region and a variable region), but other forms of antibody and derivative may be used. For example, Fabs, bi specific antibody fragments (tandem scFv-Fc, scFv-Fc knobs-into-holes, scFv-Fc-scFv, F(ab')$_2$, Fab-scFv, (Fab'scFv)$_2$, scDiabody-Fc, or scDiabody-C$_H$3), IgG-based bispecific antibodies (Hybrid hybridoma, Knobs-into-holes with common light chain, Two-in-one IgG, Dual V domain IgG, IgG-scFv, scFv-IgG, IgG-V, V-IgG), minibody, tribi-minibody, nanobodies, di-diabody.

The antibody may be human, or humanised, or chimeric.

The one or more mutations preferably comprise mutation from a non-cysteine amino acid to a cysteine amino acid. Preferably the non-cysteine amino acid is selected from serine, valine, threonine, or alanine; more preferably serine or threonine. Alternatively, the mutation may be to lysine, glutamine, or a non-natural amino acid.

In preferred embodiments, the one or more mutations is selected from S160C, T190C, S443C, S447C (on the heavy chain), T180C, or T206C (on the light chain). The numbering recited herein is positional numbering based on the full length trastuzumab sequence. Other numbering conventions are summarised in the below table:

| ADC Substitution (positional numbering) | Strands, turns and loops for C-DOMAINs | IMGT unique numbering for C-DOMAINs | CH1/CL (kappa) | | | |
|---|---|---|---|---|---|---|
| | | | IGHG1 amino acid translation | IMGT exon numbering | Eu numbering | Kabat numbering |
| H:S160C | C-strand | 40 | S | 40 | 157 | 156 |
| H:T190C | E-strand | 90 | T | 70 | 187 | 192 |
| H:S443C | G-strand | 120 | S | 100 | 440 | 471 |
| H:S447C | G-strand | 124 | S | 104 | 444 | 475 |
| L:T180C | E-strand | 90 | T | 73 | 180 | 180 |
| L:T206C | G-strand | 118 | T | 99 | 206 | 206 |

Preferred antibodies include the light chain T180 mutation. This may be the sole mutation, or may be combined with any of the other mutations disclosed herein.

Preferred antibodies comprise combinations of 2 mutations which are selected from the group of
LC T180 in combination with LC S208,
LC T180 in combination with LC S171,
LC T180 in combination with LC S182,
LC T180 in combination with LC A184,
LC T180 in combination with LC V191,
LC T180 in combination with LC S202,
LC T180 in combination with LC S203,
LC T180 in combination with LC T206,
LC T180 in combination with HC S160,
LC T180 in combination with HC T190,
LC T180 in combination with HC S443,
LC T180 in combination with HC S447,
LC T180 in combination with HC S139,
LC T180 in combination with HC S168,
LC T180 in combination with HC V170,
LC T180 in combination with HC V176,
LC T180 in combination with HC T200,
LC T180 in combination with HC S445.

The mutations are preferably mutations to cysteine, lysine, glutamine, or a non-natural amino acid.

Further preferred antibodies comprise combinations of 2 mutations selected from the group of
LC T180C in combination with LC S208C,
LC T180C in combination with LC S171C,
LC T180C in combination with LC S182C,
LC T180C in combination with LC A184C,
LC T180C in combination with LC V191C,
LC T180C in combination with LC S202C,
LC T180C in combination with LC S203C,
LC T180C in combination with LC T206C,
LC T180C in combination with HC S160C,
LC T180C in combination with HC T190C,
LC T180C in combination with HC S443C,
LC T118C in combination with HC S447C,
LC T180C in combination with HC S139C,
LC T180C in combination with HC S168C,
LC T180C in combination with HC V170C,
LC T180C in combination with HC V176C,
LC T180C in combination with HC T200C,
LC T180C in combination with HC S445C.

Most preferred antibodies comprise LC T180C in combination with HC S160C.

Other preferred antibodies comprise combinations of the 2 amino acid sequences selected from the group of:
SEQ ID No. 33 and SEQ ID No. 22,
SEQ ID No. 33 and SEQ ID No. 23,
SEQ ID No. 33 and SEQ ID No. 24,
SEQ ID No. 33 and SEQ ID No. 25,
SEQ ID No. 33 and SEQ ID No. 26,
SEQ ID No. 33 and SEQ ID No. 27,
SEQ ID No. 33 and SEQ ID No. 28,
SEQ ID No. 33 and SEQ ID No. 29,
SEQ ID No. 33 and SEQ ID No. 30,
SEQ ID No. 33 and SEQ ID No. 31,
SEQ ID No. 33 and SEQ ID No. 32,
SEQ ID No. 33 and SEQ ID No. 34,
SEQ ID No. 33 and SEQ ID No. 35,
SEQ ID No. 33 and SEQ ID No. 36,
SEQ ID No. 33 and SEQ ID No. 37,
SEQ ID No. 33 and SEQ ID No. 38,
SEQ ID No. 33 and SEQ ID No. 39,
SEQ ID No. 33 and SEQ ID No. 40.

In preferred antibodies, X is cysteine. Alternatively, X may be independently selected from lysine, glutamine, cysteine, or a non-natural amino acid, and is most preferably cysteine.

Most preferred antibodies comprise SEQ ID No. 33 and SEQ ID No. 23.

Additional mutations which may be combined with any of the aspects disclosed herein include:

| Engineered Cysteine (Kabat) | Cys (Positional No.) | Sequence | SEQ ID No: |
|---|---|---|---|
| Heavy chain | | | |
| S134C | S139 | FPLAPSSKST$\underline{X}$GGTAALGCLV | 22 |
| S156C | S160 | KDYFPEPVTV$\underline{X}$WNSGALTSGV | 23 |
| S168C | S168 | TVSWNSGALT$\underline{X}$GVHTFPAVLQ | 24 |
| V171C | V170 | SWNSGALTSG$\underline{X}$HTFPAVLQSS | 25 |
| V177C | V176 | LTSGVHTFPA$\underline{X}$LQSSGLYSLS | 26 |
| T192C | T190 | SGLYSLSSVV$\underline{X}$VPSSSLGTQT | 27 |
| T205C | T200 | TVPSSSLGTQ$\underline{X}$YICNVNHKPS | 28 |
| S471C | S443 | EALHNHYTQK$\underline{X}$LSLSPGK | 29 |
| S473C | S445 | EALHNHYTQKSL$\underline{X}$LSPGK | 30 |
| S475C | S447 | EALHNHYTQKSLSL$\underline{X}$PGK | 31 |
| Light chain | | | |
| S171C | S171 | ESVTEQDSKD$\underline{X}$TYSLSSTLTL | 32 |
| T180C | T180 | DSTYSLSSTL$\underline{X}$LSKADYEKHK | 33 |
| S182C | S182 | TYSLSSTLTL$\underline{X}$KADYEKHKVY | 34 |
| A184C | A184 | SLSSTLTLSK$\underline{X}$DYEKHKVYAC | 35 |
| V191C | V191 | LSKADYEKHK$\underline{X}$YACEVTHQGL | 36 |
| S202C | S202 | YACEVTHQGL$\underline{X}$SPVTKSFNRG | 37 |
| S203C | S203 | ACEVTHQGLS$\underline{X}$PVTKSFNRGE | 38 |
| T206C | T206 | VTHQGLSSPV$\underline{X}$KSFNRGEC | 39 |
| S208C | S208 | VTHQGLSSPVTK$\underline{X}$FNRGEC | 40 |

In the above table, the mutated residues are indicated as X. X is preferably cysteine, but other mutant residues may be used, in particular lysine, glutamine, or a non-natural amino acid. Note that V191 may be L191 in certain parent antibodies, in particular Kappa allotypes Km1 and Km2; where reference is made herein to V191 mutations, then unless the context requires otherwise this is understood to refer also to L191 mutations.

Other preferred antibodies include the light chain T206 mutation in combination with one or more other mutations. In preferred embodiments, the light chain T206 mutation is combined with another mutation described herein. The following are preferred combinations of two mutations; antibodies according to the invention may comprise these mutations together with one or more additional mutations.
LC T206 in combination with LC S208,
LC T206 in combination with LC S171,
LC T206 in combination with LC S182,
LC T206 in combination with LC A184, LC T206 in combination with LC V191,
LC T206 in combination with LC S202,
LC T206 in combination with LC S203,
LC T206 in combination with LC T180,
LC T206 in combination with HC S160,
LC T206 in combination with HC T190
LC T206 in combination with HC S443,
LC T206 in combination with HC S447,
LC T206 in combination with HC S139,
LC T206 in combination with HC S168,
LC T206 in combination with HC V170,
LC T206 in combination with HC V176,
LC T206 in combination with HC T200,
LC T206 in combination with HC S445.
Of which are preferred
LC T206 in combination with LC T180,
LC T206 in combination with HC S160,
LC T206 in combination with HC T190
LC T206 in combination with HC S443,
LC T206 in combination with HC S447,
Of which are most preferred
LC T206C in combination with LC T180C,
LC T206O in combination with HC S160C,
LC T206C in combination with HC T190C
LC T206C in combination with HC S443C,
LC T206O in combination with HC S447C.

Thus, preferred antibodies may comprise combinations of the amino acid sequence of SEQ ID No 39 together with an amino acid sequence selected from SEQ ID No 22 to 38 or 40. In preferred antibodies, X is cysteine. Alternatively, X may be independently selected from lysine, glutamine, cysteine, or a non-natural amino acid, and is most preferably cysteine.

Other preferred antibodies include the heavy chain S160 mutation in combination with one or more other mutations. In preferred embodiments, the heavy chain S160 mutation is combined with another mutation described herein. The following are preferred combinations of two mutations; antibodies according to the invention may comprise these mutations together with one or more additional mutations.

HC S160 in combination with LC S208,
HC S160 in combination with LC S171,
HC S160 in combination with LC S182,
HC S160 in combination with LC A184,
HC S160 in combination with LC V191,
HC S160 in combination with LC S202,
HC S160 in combination with LC S203,
HC S160 in combination with LC T180,
HC S160 in combination with LC T206,
HC S160 in combination with HC T190,
HC S160 in combination with HC S443,
HC S160 in combination with HC S447,
HC S160 in combination with HC S139,
HC S160 in combination with HC S168,
HC S160 in combination with HC V170,
HC S160 in combination with HC V176,
HC S160 in combination with HC T200,
HC S160 in combination with HC S445.
Of which are preferred
HC S160 in combination with LC T180,
HC S160 in combination with LC T206,
HC S160 in combination with HC T190,
HC S160 in combination with HC S443,
HC S160 in combination with HC S447,
Of which are most preferred
HC S160C in combination with LC T180C,
HC S160C in combination with LC T206C,
HC S160C in combination with HC T190C,
HC S160C in combination with HC S443C,
HC S160C in combination with HC S447C, Thus, preferred antibodies may comprise combinations of the amino acid sequence of SEQ ID No 23 together with an amino acid sequence selected from SEQ ID No 22 or 24 to 40. In preferred antibodies, X is cysteine. Alternatively, X may be independently selected from lysine, glutamine, cysteine, or a non-natural amino acid, and is most preferably cysteine.

Other preferred antibodies include the heavy chain T190 mutation in combination with one or more other mutations. In preferred embodiments, the heavy chain T190 mutation is combined with another mutation described herein. The following are preferred combinations of two mutations; antibodies according to the invention may comprise these mutations together with one or more additional mutations.

HC T190 in combination with LC S208,
HC T190 in combination with LC S171,
HC T190 in combination with LC S182,
HC T190 in combination with LC A184,
HC T190 in combination with LC V191,
HC T190 in combination with LC S202,
HC T190 in combination with LC S203,
HC T190 in combination with LC T180,
HC T190 in combination with LC T206,
HC T190 in combination with HC S160,
HC T190 in combination with HC S443,
HC T190 in combination with HC S447,
HC T190 in combination with HC S139,
HC T190 in combination with HC S168,
HC T190 in combination with HC V170,
HC T190 in combination with HC V176,
HC T190 in combination with HC T200,
HC T190 in combination with HC S445.
Of which are preferred
HC T190 in combination with LC T180,
HC T190 in combination with LC T206,
HC T190 in combination with HC S160,
HC T190 in combination with HC S443,
HC T190 in combination with HC S447,
Of which are most preferred
HC T190C in combination with LC T180C,
HC T190C in combination with LC T206C,
HC T190C in combination with HC S160C,
HC T190C in combination with HC S443C,
HC T190C in combination with HC S447C.

Thus, preferred antibodies may comprise combinations of the amino acid sequence of SEQ ID No 27 together with an amino acid sequence selected from SEQ ID No 22 to 26 or 28 to 40. In preferred antibodies, X is cysteine. Alternatively, X may be independently selected from lysine, glutamine, cysteine, or a non-natural amino acid, and is most preferably cysteine.

Other preferred antibodies include the heavy chain S443 mutation in combination with one or more other mutations. In preferred embodiments, the heavy chain S443 mutation is combined with another mutation described herein. The following are preferred combinations of two mutations; antibodies according to the invention may comprise these mutations together with one or more additional mutations.

HC S443 in combination with LC S208,
HC S443 in combination with LC S171,
HC S443 in combination with LC S182,
HC S443 in combination with LC A184,
HC S443 in combination with LC V191,
HC S443 in combination with LC S202, HC S443 in combination with LC S203,
HC S443 in combination with LC T180,
HC S443 in combination with LC T206,
HC S443 in combination with HC S160,
HC S443 in combination with HC T190,
HC S443 in combination with HC S447,
HC S443 in combination with HC S139,
HC S443 in combination with HC S168,
HC S443 in combination with HC V170,
HC S443 in combination with HC V176,
HC S443 in combination with HC T200,
HC S443 in combination with HC S445.
Of which are preferred
HC S443 in combination with LC T180,
HC S443 in combination with LC T206,
HC S443 in combination with HC S160,
HC S443 in combination with HC T190,
HC S443 in combination with HC S447,
Of which are most preferred
HC S443C in combination with LC T180C,
HC S443C in combination with LC T206C,
HC S443C in combination with HC S160C,
HC S443C in combination with HC T190C,
HC S443C in combination with HC S447C.

Thus, preferred antibodies may comprise combinations of the amino acid sequence of SEQ ID No 29 together with an amino acid sequence selected from SEQ ID No 22 to 28 or 30 to 40. In preferred antibodies, X is cysteine. Alternatively, X may be independently selected from lysine, glutamine, cysteine, or a non-natural amino acid, and is most preferably cysteine.

Other preferred antibodies include the heavy chain S447 mutation in combination with one or more other mutations. In preferred embodiments, the heavy chain S447 mutation is combined with another mutation described herein. The following are preferred combinations of two mutations; antibodies according to the invention may comprise these mutations together with one or more additional mutations.

HC S447 in combination with LC S208,
HC S447 in combination with LC S171,
HC S447 in combination with LC S182,
HC S447 in combination with LC A184,
HC S447 in combination with LC V191,
HC S447 in combination with LC S202,
HC S447 in combination with LC S203,
HC S447 in combination with LC T180,
HC S447 in combination with LC T206,
HC S447 in combination with HC S160,
HC S447 in combination with HC T190,
HC S447 in combination with HC S443,
HC S447 in combination with HC S139,
HC S447 in combination with HC S168,
HC S447 in combination with HC V170,
HC S447 in combination with HC V176,
HC S447 in combination with HC T200,
HC S447 in combination with HC S445.
Of which are preferred
HC S447 in combination with LC T180,
HC S447 in combination with, LC T206,
HC S447 in combination with HC S160,
HC S447 in combination with HC T190,
HC S447 in combination with HC S443,
Of which are most preferred
HC S447C in combination with LC T180C,
HC S447C in combination with LC T206C,
HC S447C in combination with HC S160C,
HC S447C in combination with HC T190C,
HC S447C in combination with HC S443C.

Thus, preferred antibodies may comprise combinations of the amino acid sequence of SEQ ID No 31 together with an amino acid sequence selected from SEQ ID No 22 to 30 or 32 to 40. In preferred antibodies, X is cysteine. Alternatively, X may be independently selected from lysine, glutamine, cysteine, or a non-natural amino acid, and is most preferably cysteine.

Other preferred antibodies include the light chain S208 mutation in combination with one or more other mutations. In preferred embodiments, the light chain S208 mutation is combined with another mutation described herein. The following are preferred combinations of two mutations; antibodies according to the invention may comprise these mutations together with one or more additional mutations.

LC S208 in combination with LC S171,
LC S208 in combination with LC S182,
LC S208 in combination with LC A184,
LC S208 in combination with LC V191,
LC S208 in combination with LC S202,
LC S208 in combination with LC S203,
LC S208 in combination with LC T180,
LC S208 in combination with LC T206,
LC S208 in combination with HC S160,
LC S208 in combination with HC T190,
LC S208 in combination with HC S443,
LC S208 in combination with HC S447,
LC S208 in combination with HC S139,
LC S208 in combination with HC S168,
LC S208 in combination with HC V170,
LC S208 in combination with HC V176,
LC S208 in combination with HC T200,
LC S208 in combination with HC S445.
Of which are preferred
LC S208 in combination with LC T180,
LC S208 in combination with LC T206,
LC S208 in combination with HC S160,
LC S208 in combination with HC T190,
LC S208 in combination with HC S443,
LC S208 in combination with HC S447,
Of which are most preferred
LC S208C in combination with LC T180C,
LC S208C in combination with LC T206C,
LC S208C in combination with HC S160C,
LC S208C in combination with HC T190C,
LC S208C in combination with HC S443C,
LC S208C in combination with HC S447C.

Thus, preferred antibodies may comprise combinations of the amino acid sequence of SEQ ID No 40 together with an amino acid sequence selected from SEQ ID No 22 to 39. In preferred antibodies, X is cysteine. Alternatively, X may be independently selected from lysine, glutamine, cysteine, or a non-natural amino acid, and is most preferably cysteine.

Accordingly, preferred antibodies comprise combinations of the 2 amino acid sequences selected from the group of:
SEQ ID No. 40 and SEQ ID No. 22,
SEQ ID No. 40 and SEQ ID No. 23,
SEQ ID No. 40 and SEQ ID No. 24,
SEQ ID No. 40 and SEQ ID No. 25,
SEQ ID No. 40 and SEQ ID No. 26,
SEQ ID No. 40 and SEQ ID No. 27,
SEQ ID No. 40 and SEQ ID No. 28,
SEQ ID No. 40 and SEQ ID No. 29,
SEQ ID No. 40 and SEQ ID No. 30,
SEQ ID No. 40 and SEQ ID No. 31,
SEQ ID No. 40 and SEQ ID No. 32, SEQ ID No. 40 and SEQ ID No. 33,
SEQ ID No. 40 and SEQ ID No. 34,
SEQ ID No. 40 and SEQ ID No. 35,
SEQ ID No. 40 and SEQ ID No. 36,
SEQ ID No. 40 and SEQ ID No. 37,
SEQ ID No. 40 and SEQ ID No. 38,
SEQ ID No. 40 and SEQ ID No. 39.

In preferred antibodies, X is cysteine. Alternatively, X may be independently selected from lysine, glutamine, cysteine, or a non-natural amino acid, and is most preferably cysteine.

Other preferred antibodies include the light chain S171 mutation in combination with one or more other mutations. In preferred embodiments, the light chain S171 mutation is combined with another mutation described herein. The following are preferred combinations of two mutations; antibodies according to the invention may comprise these mutations together with one or more additional mutations.

LC S171 in combination with LC S208,
LC S171 in combination with LC S182,
LC S171 in combination with LC A184,
LC S171 in combination with LC V191,
LC S171 in combination with LC S202,
LC S171 in combination with LC S203,
LC S171 in combination with LC T180,
LC S171 in combination with LC T206,
LC S171 in combination with HC S160,
LC S171 in combination with HC T190,
LC S171 in combination with HC S443,
LC S171 in combination with HC S447,
LC S171 in combination with HC S139,
LC S171 in combination with HC S168,
LC S171 in combination with HC V170,
LC S171 in combination with HC V176,
LC S171 in combination with HC T200,
LC S171 in combination with HC S445.
Of which are preferred
LC S171 in combination with LC T180,
LC S171 in combination with LC T206,
LC S171 in combination with HC S160,
LC S171 in combination with HC T190,
LC S171 in combination with HC S443,
LC S171 in combination with HC S447,
Of which are most preferred
LC S171C in combination with LC T180C,
LC S171C in combination with LC T206C,
LC S171C in combination with HC S160C,
LC S171C in combination with HC T190C,
LC S171C in combination with HC S443C,
LC S171C in combination with HC S447C.

Thus, preferred antibodies may comprise combinations of the amino acid sequence of SEQ ID No 32 together with an amino acid sequence selected from SEQ ID No 22 to 31 or 33 to 40. In preferred antibodies, X is cysteine. Alternatively, X may be independently selected from lysine, glutamine, cysteine, or a non-natural amino acid, and is most preferably cysteine.

Other preferred antibodies include the light chain S182 mutation in combination with one or more other mutations. In preferred embodiments, the light chain S182 mutation is combined with another mutation described herein. The following are preferred combinations of two mutations; antibodies according to the invention may comprise these mutations together with one or more additional mutations.

LC S182 in combination with LC S208,
LC S182 in combination with LC S171,
LC S182 in combination with LC A184,
LC S182 in combination with LC V191,
LC S182 in combination with LC S202,
LC S182 in combination with LC S203,
LC S182 in combination with LC T180,
LC S182 in combination with LC T206,
LC S182 in combination with HC S160,
LC S182 in combination with HC T190,
LC S182 in combination with HC S443,
LC S182 in combination with HC S447,
LC S182 in combination with HC S139,
LC S182 in combination with HC S168,
LC S182 in combination with HC V170,
LC S182 in combination with HC V176,
LC S182 in combination with HC T200,
LC S182 in combination with HC S445.
Of which are preferred
LC S182 in combination with LC T180,
LC S182 in combination with LC T206,
LC S182 in combination with HC S160,
LC S182 in combination with HC T190,
LC S182 in combination with HC S443,
LC S182 in combination with HC S447,
Of which are most preferred
LC S182C in combination with LC T180C,
LC S182C in combination with LC T206C,
LC S182C in combination with HC S160C,
LC S182C in combination with HC T190C,
LC S182C in combination with HC S443C,
LC S182C in combination with HC S447C.

Thus, preferred antibodies may comprise combinations of the amino acid sequence of SEQ ID No 34 together with an amino acid sequence selected from SEQ ID No 22 to 33 or 35 to 40. In preferred antibodies, X is cysteine. Alternatively, X may be independently selected from lysine, glutamine, cysteine, or a non-natural amino acid, and is most preferably cysteine.

Other preferred antibodies include the light chain A184 mutation in combination with one or more other mutations. In preferred embodiments, the light chain A184 mutation is combined with another mutation described herein. The following are preferred combinations of two mutations; antibodies according to the invention may comprise these mutations together with one or more additional mutations.

LC A184 in combination with LC S208,
LC A184 in combination with LC S171,
LC A184 in combination with LC S182,
LC A184 in combination with LC V191,
LC A184 in combination with LC S202,
LC A184 in combination with LC S203,
LC A184 in combination with LC T180,
LC A184 in combination with LC T206,
LC A184 in combination with HC S160,
LC A184 in combination with HC T190,
LC A184 in combination with HC S443,
LC A184 in combination with HC S447,
LC A184 in combination with HC S139,
LC A184 in combination with HC S168,
LC A184 in combination with HC V170,
LC A184 in combination with HC V176,
LC A184 in combination with HC T200,
LC A184 in combination with HC S445.
Of which are preferred
LC A184 in combination with LC T180,
LC A184 in combination with LC T206,
LC A184 in combination with HC S160,
LC A184 in combination with HC T190, LC A184 in combination with HC S443,
LC A184 in combination with HC S447,
Of which are most preferred
LC A184C in combination with LC T180C,
LC A184C in combination with LC T206C,
LC A184C in combination with HC S160C,
LC A184C in combination with HC T190C,
LC A184C in combination with HC S443C,
LC A184C in combination with HC S447C.

Thus, preferred antibodies may comprise combinations of the amino acid sequence of SEQ ID No 35 together with an amino acid sequence selected from SEQ ID No 22 to 34 or 36 to 40. In preferred antibodies, X is cysteine. Alternatively, X may be independently selected from lysine, glutamine, cysteine, or a non-natural amino acid, and is most preferably cysteine.

Other preferred antibodies include the light chain V191 mutation in combination with one or more other mutations. In preferred embodiments, the light chain V191 mutation is combined with another mutation described herein. The following are preferred combinations of two mutations; antibodies according to the invention may comprise these mutations together with one or more additional mutations.
LC V191 in combination with LC S208,
LC V191 in combination with LC S171,
LC V191 in combination with LC S182,
LC V191 in combination with LC A184,
LC V191 in combination with LC S202,
LC V191 in combination with LC S203,
LC V191 in combination with LC T180,
LC V191 in combination with LC T206,
LC V191 in combination with HC S160,
LC V191 in combination with HC T190,
LC V191 in combination with HC S443,
LC V191 in combination with HC S447,
LC V191 in combination with HC S139,
LC V191 in combination with HC S168,
LC V191 in combination with HC V170,
LC V191 in combination with HC V176,
LC V191 in combination with HC T200,
LC V191 in combination with HC S445.
Of which are preferred
LC V191 in combination with LC T180,
LC V191 in combination with LC T206,
LC V191 in combination with HC S160,
LC V191 in combination with HC T190,
LC V191 in combination with HC S443,
LC V191 in combination with HC S447,
Of which are most preferred
LC V191C in combination with LC T180C,
LC V191C in combination with LC T206C,
LC V191C in combination with HC S160C,
LC V191C in combination with HC T190C,
LC V191C in combination with HC S443C,
LC V191C in combination with HC S447C.

Thus, preferred antibodies may comprise combinations of the amino acid sequence of SEQ ID No 36 together with an amino acid sequence selected from SEQ ID No 22 to 35 or 37 to 40. In preferred antibodies, X is cysteine. Alternatively, X may be independently selected from lysine, glutamine, cysteine, or a non-natural amino acid, and is most preferably cysteine.

Other preferred antibodies include the light chain S202 mutation in combination with one or more other mutations. In preferred embodiments, the light chain S202 mutation is combined with another mutation described herein. The following are preferred combinations of two mutations; antibodies according to the invention may comprise these mutations together with one or more additional mutations.
LC S202 in combination with LC S208,
LC S202 in combination with LC S171,
LC S202 in combination with LC S182,
LC S202 in combination with LC A184,
LC S202 in combination with LC V191,
LC S202 in combination with LC S203,
LC S202 in combination with LC T180,
LC S202 in combination with LC T206,
LC S202 in combination with HC S160,
LC S202 in combination with HC T190,
LC S202 in combination with HC S443,
LC S202 in combination with HC S447,
LC S202 in combination with HC S139,
LC S202 in combination with HC S168,
LC S202 in combination with HC V170,
LC S202 in combination with HC V176,
LC S202 in combination with HC T200,
LC S202 in combination with HC S445.
Of which are preferred
LC S202 in combination with LC T180,
LC S202 in combination with LC T206,
LC S202 in combination with HC S160,
LC S202 in combination with HC T190,
LC S202 in combination with HC S443,
LC S202 in combination with HC S447,
Of which are most preferred
LC S202C in combination with LC T180C,
LC S202C in combination with LC T206C,
LC S202C in combination with HC S160C,
LC S202C in combination with HC T190C,
LC S202C in combination with HC S443C,
LC S202C in combination with HC S447C.

Thus, preferred antibodies may comprise combinations of the amino acid sequence of SEQ ID No 37 together with an amino acid sequence selected from SEQ ID No 22 to 36 or 38 to 40. In preferred antibodies, X is cysteine. Alternatively, X may be independently selected from lysine, glutamine, cysteine, or a non-natural amino acid, and is most preferably cysteine.

Other preferred antibodies include the light chain S203 mutation in combination with one or more other mutations. In preferred embodiments, the light chain S203 mutation is combined with another mutation described herein. The following are preferred combinations of two mutations; antibodies according to the invention may comprise these mutations together with one or more additional mutations.
LC S203 in combination with LC S208,
LC S203 in combination with LC S171,
LC S203 in combination with LC S182,
LC S203 in combination with LC A184,
LC S203 in combination with LC V191,
LC S203 in combination with LC S202,
LC S203 in combination with LC T180,
LC S203 in combination with LC T206,
LC S203 in combination with HC S160,
LC S203 in combination with HC T190,
LC S203 in combination with HC S443,
LC S203 in combination with HC S447,
LC S203 in combination with HC S139,
LC S203 in combination with HC S168,
LC S203 in combination with HC V170,
LC S203 in combination with HC V176,
LC S203 in combination with HC T200,
LC S203 in combination with HC S445.

Of which are preferred
LC S203 in combination with LC T180,
LC S203 in combination with LC T206,
LC S203 in combination with HC S160,
LC S203 in combination with HC T190,
LC S203 in combination with HC S443,
LC S203 in combination with HC S447,
Of which are most preferred
LC S203C in combination with LC T180C,
LC S203C in combination with LC T206C,
LC S203C in combination with HC S160C,
LC S203C in combination with HC T190C,
LC S203C in combination with HC S443C,
LC S203C in combination with HC S447C.

Thus, preferred antibodies may comprise combinations of the amino acid sequence of SEQ ID No 38 together with an amino acid sequence selected from SEQ ID No 22 to 37 or 39 to 40. In preferred antibodies, X is cysteine. Alternatively, X may be independently selected from lysine, glutamine, cysteine, or a non-natural amino acid, and is most preferably cysteine.

Other preferred antibodies include the heavy chain S139 mutation in combination with one or more other mutations. In preferred embodiments, the heavy chain S139 mutation is combined with another mutation described herein. The following are preferred combinations of two mutations; antibodies according to the invention may comprise these mutations together with one or more additional mutations.
HC S139 in combination with LC S208,
HC S139 in combination with LC S171,
HC S139 in combination with LC S182,
HC S139 in combination with LC A184,
HC S139 in combination with LC V191,
HC S139 in combination with LC S202,
HC S139 in combination with LC S203,
HC S139 in combination with LC T180,
HC S139 in combination with LC T206,
HC S139 in combination with HC S160,
HC S139 in combination with HC T190,
HC S139 in combination with HC S443,
HC S139 in combination with HC S447,
HC S139 in combination with HC S168,
HC S139 in combination with HC V170,
HC S139 in combination with HC V176,
HC S139 in combination with HC T200,
HC S139 in combination with HC S445.
Of which are preferred
HC S139 in combination with LC T180,
HC S139 in combination with LC T206,
HC S139 in combination with HC S160,
HC S139 in combination with HC T190,
HC S139 in combination with HC S443,
HC S139 in combination with HC S447,
Of which are most preferred
HC S139C in combination with LC T180C,
HC S139C in combination with LC T206C,
HC S139C in combination with HC S160C,
HC S139C in combination with HC T190C,
HC S139C in combination with HC S443C,
HC S139C in combination with HC S447C.

Thus, preferred antibodies may comprise combinations of the amino acid sequence of SEQ ID No 22 together with an amino acid sequence selected from SEQ ID No 23 to 40. In preferred antibodies, X is cysteine. Alternatively, X may be independently selected from lysine, glutamine, cysteine, or a non-natural amino acid, and is most preferably cysteine.

Other preferred antibodies include the heavy chain S168 mutation in combination with one or more other mutations. In preferred embodiments, the heavy chain S168 mutation is combined with another mutation described herein. The following are preferred combinations of two mutations; antibodies according to the invention may comprise these mutations together with one or more additional mutations.
HC S168 in combination with LC S208,
HC S168 in combination with LC S171,
HC S168 in combination with LC S182,
HC S168 in combination with LC A184,
HC S168 in combination with LC V191,
HC S168 in combination with LC S202,
HC S168 in combination with LC S203,
HC S168 in combination with LC T180,
HC S168 in combination with LC T206,
HC S168 in combination with HC S160,
HC S168 in combination with HC T190,
HC S168 in combination with HC S443,
HC S168 in combination with HC S447,
HC S168 in combination with HC S139,
HC S168 in combination with HC V170,
HC S168 in combination with HC V176,
HC S168 in combination with HC T200,
HC S168 in combination with HC S445.
Of which are preferred
HC S168 in combination with LC T180,
HC S168 in combination with LC T206,
HC S168 in combination with HC S160,
HC S168 in combination with HC T190,
HC S168 in combination with HC S443,
HC S168 in combination with HC S447,
Of which are most preferred
HC S168C in combination with LC T180C,
HC S168C in combination with LC T206C,
HC S168C in combination with HC S160C,
HC S168C in combination with HC T190C,
HC S168C in combination with HC S443C,
HC S168C in combination with HC S447C.

Thus, preferred antibodies may comprise combinations of the amino acid sequence of SEQ ID No 24 together with an amino acid sequence selected from SEQ ID No 22, 23, or 25 to 40. In preferred antibodies, X is cysteine. Alternatively, X may be independently selected from lysine, glutamine, cysteine, or a non-natural amino acid, and is most preferably cysteine.

Other preferred antibodies include the heavy chain V170 mutation in combination with one or more other mutations. In preferred embodiments, the heavy chain V170 mutation is combined with another mutation described herein. The following are preferred combinations of two mutations; antibodies according to the invention may comprise these mutations together with one or more additional mutations.
HC V170 in combination with LC S208,
HC V170 in combination with LC S171,
HC V170 in combination with LC S182,
HC V170 in combination with LC A184,
HC V170 in combination with LC V191,
HC V170 in combination with LC S202,
HC V170 in combination with LC S203,
HC V170 in combination with LC T180,
HC V170 in combination with LC T206,
HC V170 in combination with HC S160,
HC V170 in combination with HC T190,
HC V170 in combination with HC S443,
HC V170 in combination with HC S447,
HC V170 in combination with HC S139, HC V170 in combination with HC S168,
HC V170 in combination with HC V176,
HC V170 in combination with HC T200,
HC V170 in combination with HC S445.
Of which are preferred
HC V170 in combination with LC T180,
HC V170 in combination with LC T206,
HC V170 in combination with HC S160,
HC V170 in combination with HC T190,
HC V170 in combination with HC S443,
HC V170 in combination with HC S447,
Of which are most preferred
HC V170C in combination with LC T180C,
HC V170C in combination with LC T206C,
HC V170C in combination with HC S160C,
HC V170C in combination with HC T190C,
HC V170C in combination with HC S443C,
HC V170C in combination with HC S447C.

Thus, preferred antibodies may comprise combinations of the amino acid sequence of SEQ ID No 25 together with an amino acid sequence selected from SEQ ID No 22 to 24 or 26 to 40. In preferred antibodies, X is cysteine. Alternatively, X may be independently selected from lysine, glutamine, cysteine, or a non-natural amino acid, and is most preferably cysteine.

Other preferred antibodies include the heavy chain V176 mutation in combination with one or more other mutations. In preferred embodiments, the heavy chain V176 mutation is combined with another mutation described herein. The following are preferred combinations of two mutations; antibodies according to the invention may comprise these mutations together with one or more additional mutations.

HC V176 in combination with LC S208,
HC V176 in combination with LC S171,
HC V176 in combination with LC S182,
HC V176 in combination with LC A184,
HC V176 in combination with LC V191,
HC V176 in combination with LC S202,
HC V176 in combination with LC S203,
HC V176 in combination with LC T180,
HC V176 in combination with LC T206,
HC V176 in combination with HC S160,
HC V176 in combination with HC T190,
HC V176 in combination with HC S443,
HC V176 in combination with HC S447,
HC V176 in combination with HC S139,
HC V176 in combination with HC S168,
HC V176 in combination with HC V170,
HC V176 in combination with HC T200,
HC V176 in combination with HC S445.
Of which are preferred
HC V176 in combination with LC T180,
HC V176 in combination with LC T206,
HC V176 in combination with HC S160,
HC V176 in combination with HC T190,
HC V176 in combination with HC S443,
HC V176 in combination with HC S447,
Of which are most preferred
HC V176C in combination with LC T180C,
HC V176C in combination with LC T206C,
HC V176C in combination with HC S160C,
HC V176C in combination with HC T190C,
HC V176C in combination with HC S443C,
HC V176C in combination with HC S447C.

Thus, preferred antibodies may comprise combinations of the amino acid sequence of SEQ ID No 26 together with an amino acid sequence selected from SEQ ID No 22 to 25 or 27 to 40. In preferred antibodies, X is cysteine. Alternatively, X may be independently selected from lysine, glutamine, cysteine, or a non-natural amino acid, and is most preferably cysteine.

Other preferred antibodies include the heavy chain T200 mutation in combination with one or more other mutations. In preferred embodiments, the heavy chain T200 mutation is combined with another mutation described herein. The following are preferred combinations of two mutations; antibodies according to the invention may comprise these mutations together with one or more additional mutations.

HC T200 in combination with LC S208,
HC T200 in combination with LC S171,
HC T200 in combination with LC S182,
HC T200 in combination with LC A184,
HC T200 in combination with LC V191,
HC T200 in combination with LC S202,
HC T200 in combination with LC S203,
HC T200 in combination with LC T180,
HC T200 in combination with LC T206,
HC T200 in combination with HC S160,
HC T200 in combination with HC T190,
HC T200 in combination with HC S443,
HC T200 in combination with HC S447,
HC T200 in combination with HC S139,
HC T200 in combination with HC S168,
HC T200 in combination with HC V170,
HC T200 in combination with HC V176,
HC T200 in combination with HC S445.
Of which are preferred
HC T200 in combination with LC T180,
HC T200 in combination with LC T206,
HC T200 in combination with HC S160,
HC T200 in combination with HC T190,
HC T200 in combination with HC S443,
HC T200 in combination with HC S447,
Of which are most preferred
HC T200C in combination with LC T180C,
HC T200C in combination with LC T206C,
HC T200C in combination with HC S160C,
HC T200C in combination with HC T190C,
HC T200C in combination with HC S443C,
HC T200C in combination with HC S447C.

Thus, preferred antibodies may comprise combinations of the amino acid sequence of SEQ ID No 28 together with an amino acid sequence selected from SEQ ID No 22 to 27 or 29 to 40. In preferred antibodies, X is cysteine. Alternatively, X may be independently selected from lysine, glutamine, cysteine, or a non-natural amino acid, and is most preferably cysteine.

Other preferred antibodies include the heavy chain S445 mutation in combination with one or more other mutations. In preferred embodiments, the heavy chain S445 mutation is combined with another mutation described herein. The following are preferred combinations of two mutations; antibodies according to the invention may comprise these mutations together with one or more additional mutations.

HC S445 in combination with LC S208,
HC S445 in combination with LC S171,
HC S445 in combination with LC S182,
HC S445 in combination with LC A184,
HC S445 in combination with LC V191,
HC S445 in combination with LC S202,
HC S445 in combination with LC S203,
HC S445 in combination with LC 1180,
HC S445 in combination with LC T206,
HC S445 in combination with HC S160, HC S445 in combination with HC T190,
HC S445 in combination with HC S443,
HC S445 in combination with HC S447,
HC S445 in combination with HC S139,
HC S445 in combination with HC S168,
HC S445 in combination with HC V170,
HC S445 in combination with HC V176,
HC S445 in combination with HC T200.
Of which are preferred
HC S445 in combination with LC T180,
HC S445 in combination with LC T206,
HC S445 in combination with HC S160,
HC S445 in combination with HC T190,
HC S445 in combination with HC S443,
HC S445 in combination with HC S447,
Of which are most preferred
HC S445C in combination with LC T180C,
HC S445C in combination with LC T206C,
HC S445C in combination with HC S160C,
HC S445C in combination with HC T190C,
HC S445C in combination with HC S443C,
HC S445C in combination with HC S447C.

Thus, preferred antibodies may comprise combinations of the amino acid sequence of SEQ ID No 30 together with an amino acid sequence selected from SEQ ID No 22 to 29 or 31 to 40. In preferred antibodies, X is cysteine. Alternatively, X may be independently selected from lysine, glutamine, cysteine, or a non-natural amino acid, and is most preferably cysteine.

The antibody may be selected from Abciximab; Rituximab; Basiliximab; Daclizumab; Palivizumab; Infliximab; Trastuzumab; Alemtuzumab; Adalimumab; Efalizumab; Cetuximab; Ibritumomab; Omalizumab; Bevacizumab; Ranibizumab; Golimumab; Canakinumab; Ustekinumab; Tocilizumab; Ofatumumab; Belimumab; Ipilimumab; Brentuximab; Pertuzumab; Raxibacumab; Vedolizumab; Ramucirumab; Obinutuzumab; Siltuximab; Secukinumab; Dinutuximab.

The invention further provides an antibody having a light chain comprising or consisting of the amino acid sequence of SEQ ID NO 1, and a heavy chain comprising or consisting of an amino acid sequence selected from any of SEQ ID NO 3 to 12. Alternatively the antibody has a light chain comprising or consisting of an amino acid sequence selected from SEQ ID NO 13 to 21, and a heavy chain comprising or consisting of the amino acid sequence of SEQ ID NO 2. The antibody preferably has two light chains and two heavy chains.

Also provided is an antibody having a variable region providing binding specificity to a target, and a constant region, wherein the constant region comprises a light chain constant region having the amino acid sequence of residues 109 to 214 of SEQ ID NO 1, and a heavy chain constant region having the amino acid sequence of residues 121 to 450 of a sequence selected from SEQ ID NO 3 to 12. Alternatively, the constant region comprises a light chain constant region having the amino acid sequence of residues 109 to 214 of SEQ ID NO 13 to 21, and a heavy chain constant region having the amino acid sequence of residues 121 to 450 of SEQ ID NO 2. Preferably, the antibody comprises a light chain constant region having the amino acid sequence of residues 109 to 214 of SEQ ID NO 14, and a heavy chain constant region having the amino acid sequence of residues 121 to 450 of SEQ ID NO 2; or the antibody comprises a light chain constant region having the amino acid sequence of residues 109 to 214 of SEQ ID NO 14, and a heavy chain constant region having the amino acid sequence of residues 121 to 450 of SEQ ID NO 4; or the antibody comprises a light chain constant region having the amino acid sequence of residues 109 to 214 of SEQ ID NO 21, and a heavy chain constant region having the amino acid sequence of residues 121 to 450 of SEQ ID NO 2.

Also provided is an antibody-drug conjugate (ADC), comprising an antibody according to the first aspect of the invention, conjugated to a payload, preferably a drug payload, such that the DAR is from 1.7-2.2 in case of one mutation on either heavy or light chain and a DAR of 3.4-4.4 in case of 2 mutations in light or heavy chain or one in light and one in heavy chain.

The drug payload may be a microtubule disrupting agent, or a DNA modifying agent. Examples of suitable drug payloads include dolastatin, vedotin, monomethyl auristatin F, maytansinoids including DM1 and DM4, duocarmycin analogs, calicheamicin, pyrrolobenzodiazepines, duocarmycin, centanamycin, irinotecan, and doxorubicin. Other drug payloads may be used.

A yet further aspect of the invention provides an antibody or an ADC as herein described, for use as a therapeutic. The invention also provides a pharmaceutical composition comprising an antibody or an ADC as herein described. A further aspect of the invention provides a method for generating an ADC, the method comprising conjugating an antibody as herein described to a drug payload.

Another aspect of the invention provides a method for improving a selected characteristic of a parent antibody after conjugation of the antibody to a payload, wherein the improvement is selected from a reduction in loss of monomers, reduction in antibody fragmentation, and/or reduction in antibody aggregation after conjugation, wherein the method comprises preparing a modified antibody having the amino acid sequence of the parent antibody with one or more substitutions in residues selected from HC T200, HC V170, HC V176, HC T190, HC S139, HC S160, HC S168, HC S443 HC S445, HC S447, LC S171C, LC T180, LC T206, LC V191, LC S202, LC S203 or LC S208. The substitution is preferably cysteine, but other mutant residues may be used, in particular lysine, glutamine, or a non-natural amino acid.

Definitions

The following terms used herein are given the following definitions:

By "fragment" is meant a portion of the full size antibody which retains the specific binding properties of the antibody. By "derivative" is meant a modified antibody or antibody fragment having one or more changes to the peptide sequence, and/or bearing one or more functional groups or one or more moieties bound thereto, which retains the specific binding properties of the antibody. A "derivative" may include post-translationally modified antibodies.

By "positional numbering", "sequential numbering" and similar terms is meant the numbering of the amino acid sequence of the peptide in which the first residue at the N terminus is designated residue number 1, and subsequent residues are sequentially numbered residue 2, 3, 4. etc. This is contrasted with Kabat or EU numbering systems for antibodies.

By "site specific conjugation sites" are meant amino acid residues within an antibody which are specifically modified in order to permit conjugation of a payload.

By "wild type" is meant an unmodified, naturally occurring, peptide or nucleic acid sequence.

By "parent antibody" is meant an antibody which is used as the basis for preparing modified antibodies.

By "non-natural amino acid" is meant to an amino acid that is not a proteinogenic amino acid, or a post-translationally modified variant thereof. In particular, the term refers to an amino acid that is not one of the 20 common amino acids.

DETAILED DESCRIPTION OF THE INVENTION

Figures 1, 2:
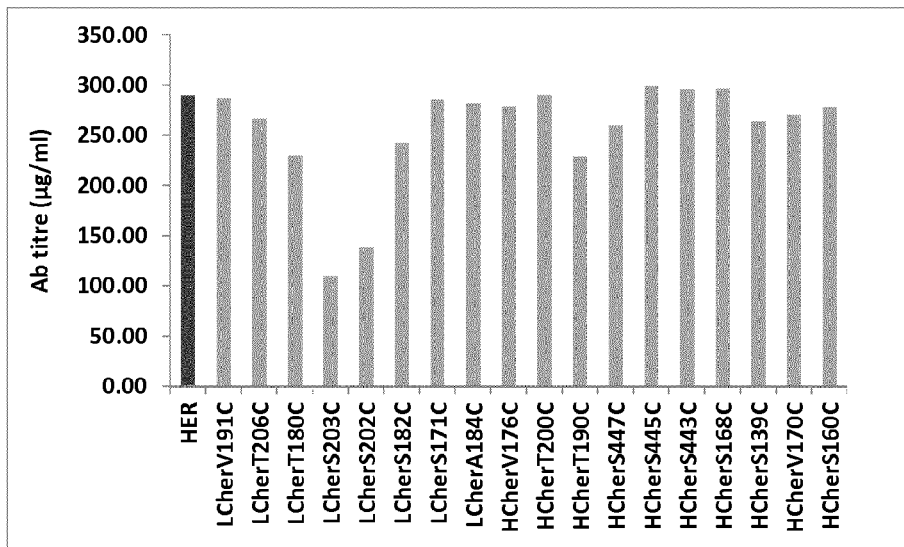
FIG. 1 shows levels of expression of candidate antibodies in 25 ml CHOK1SV cultures.
FIG. 2 shows results of SEC-HPLC analysis for % monomer of conjugated and unconjugated variant antibodies, and % aggregation and fragmentation for conjugated variants.

The present inventors have developed a process for rational design of modified antibodies to allow selection of antibodies having desired properties for production of antibodies conjugated to payloads such as for example ADCs (ADC variants). The design process incorporates in silico and in vitro screening steps. Thus, the antibodies of the present invention share a number of properties, as will be seen.

To incorporate residues for site specific conjugation, it was decided to replace native residues with another residue such as cysteine residues in selected positions of antibody structures. Candidate variants were analysed (in silico and in vitro) for desirable properties including titre and aggregation, and optionally immunogenicity (in silico only). As an initial proof of concept, Herceptin (trastuzumab) was chosen as a model antibody, and conjugation optimization and analysis carried out with biotin maleimide.

Criteria for selecting mutation sites included:
Residues to be mutated to cysteine (cys) must have similar physicochemical properties or be a small non-hydrophobic non-charged residue (ser, val, thr, ala)
Residues amenable to be mutated to cysteine must be in constant regions of either light chain ($C_K$, $C\lambda$,) or heavy chain (CH1, CH2 or CH3) of an antibody or a fragment thereof.
In cases where a modified antibody or scaffold is used, introduced cys should be at a distance >5 Å from any target-binding interface or domain to minimise risk of interfering with biological activity of the molecule.
Mutations to cys should not create intra-chain hydrogen bonds leading to the alteration of the local environment and the properties of the protein
Mutations to cys must not be placed in the interfaces between chains or domains of the antibody (or scaffold). As a general rule modifications should be at a distance >5 Å from residues involved in either chain-chain or domain-domain interfaces.
Mutations to cys should be at a distance >5 Å from any antibody native cys and should not interfere with the Fc glycosylation site (i.e. should be placed at a distance >5 Å from residue Asn295 where glycosylation occurs)
Mutations to cys should not increase the chemical degradation risk/should not introduce undesired post translational modifications Screening of the trastuzumab sequence was then carried out to identify suitable sites for mutation to another residue such as e.g. cysteine.

The unmodified light chain sequence is:

(SEQ ID NO: 1)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The unmodified heavy chain sequence is:

(SEQ ID NO: 2)
EVQLVESGGGLVQPGGSLRLSCAASGFNIKDTYIHWVRQAPGKGLEWVAR

IYPINGYTRYADSVKGRFTISADTSKNTAYLQMNSLRAEDTAVYYQSRWG

GDGFYAMDYWGQGTLVTVSSASTKGPSVFPLAPSSKSTSGGTAALGCLVK

DYFPEPVTVSWNSGALTSGVHTFFAVEQSSGLYSLSSVVTVPSSSLGTQT

YICNVNHKPSNTKVDKKVEPKSCDKTHTCPPCPAPELLGGPSVFLEPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

Ser, Thr, Val, and Ala residues in CH1, CH3, and CL were explored. This gave a number of candidates:
Light: SER171, VAL191, SER208, SER182, THR180, THR206, ALA184, SER203, SER202
Heavy: VAL170, VAL176, THR190, SER445, SER443, SER139, SER160, SER447, THR200, SER168.

These mutations were then analysed for desirable properties. Solvent accessibility surface modelling was carried out in silico. Discovery Studio (Accelrys Software Inc., Discovery Studio Modeling Environment, Release 4.0, San Diego: Accelrys Software Inc., 2013.) was used to calculate the Side Chain Solvent Accessibility Surface of the chosen residues. Solvent accessibility should be greater than 15% (>15%), or greater than 17% (>17%) to facilitate 'conjugability' of the molecule. The percentage side chain solvent accessibility surface is calculated as 100 times the side chain solvent accessibility divided by the side chain solvent accessibility of the fully exposed amino acid residue calculated using the extended Ala-X-Ala tripeptide, where X is the residue of interest. Side chains with solvent accessibility ratios of equal to or less than 15% (<=15%) or equal to or less than 17% (<=17%) are considered buried and not taken into account. The results of the SAS modelling are shown below:

| Variant LC | % SAS | Variant HC | % SAS |
|---|---|---|---|
| SER171 | 5.45 | VAL170 | 17.74 |
| VAL191 | 48.069 | VAL176 | 25.179 |
| SER208 | 48.585 | THR190 | 27.548 |
| SER182 | 67.216 | SER445 | 33.961 |
| THR180 | 67.518 | SER443 | 46.173 |
| THR206 | 75.247 | SER139 | 53.401 |
| ALA184 | 116.94 | SER160 | 61.951 |
| SER203 | 122.689 | SER447 | 72.323 |
| SER202 | 136.452 | THR200 | 91.354 |
|  |  | SER168 | 133.127 |

Aggregation propensity modelling was also carried out in silico. Aggregation propensity should not be significantly increased by the introduction of the intended engineered Cys of any of these (potential) ADC variants. This propensity will be calculated based on a Z score comparison of the reference molecule and any of the (potential) ADC variants described above to the distribution of values for a reference set of the smallest functional domain of the antibody or protein where the mutation to Cys is introduced. A mean and standard deviation is determined for the reference set. The Z-score is then calculated by subtracting the reference mean from the target proteins score and dividing by the standard deviation. The result is a zero (0) centred score where positive values indicated that the target is more aggregation prone (in this case) than the mean. Targets with a Z-score within (−1, 1) are within the standard deviation of the score within the reference set. The AggreSolve™ in silico platform (Lonza, Basel, Switzerland) comprises a collection of algorithms which, based on sequence and structural parameters, can calculate predictors that reflect the aggregation propensity of a given polypeptide. Such predictors reflect global and local (residue-specific) aggregation propensities as well as local flexibility and stability.

| Antibody Name | Z-score | Difference (Variant − WT) |
|---|---|---|
| Trastuzumab Heavy Chain (H) | 0.36 |  |
| H:S160C | 0.02 | −0.34 |
| H:T190C | 0.36 | 0.00 |
| H:S443C | 0.19 | −0.17 |
| H:S447C | 0.19 | −0.17 |
| Trastuzumab Light Chain (L) | 3.09 |  |
| L:T180C | 2.85 | −0.24 |
| L:T206C | 3.10 | 0.01 |
| Trastuzumab Heavy Chain constant domain 1 (CH1) | 0.77 |  |
| CH1:S160C | 0.17 | −0.60 |
| CH1:T190C | 0.80 | 0.04 |
| Trastuzumab Heavy Chain constant domain 3 (CH3) | −0.07 |  |
| CH3:S443C | −0.33 | −0.26 |
| CH3:S447C | −0.36 | −0.29 |
| Trastuzumab Light Chain constant domain (CL) | 1.95 |  |
| CL:T180C | 1.66 | −0.29 |
| CL:T206C | 1.98 | 0.03 |

The AggreSolve Z-score has been calculated for the full length Trastuzumab heavy and light chain, as well as for the CH1, CH3, and CL domains in which the ADC substitutions are located (the minimal functional domains).

The boundaries for the CH1, CH3 and CL domains are as per the IMGT definition in M. P. Lefranc, C. Pommie, Q. Kaas, E. Duprat, N. Bosc, D. Guiraudou, C. Jean, M. Ruiz, I. Da Piedade, M. Rouard, E. Foulquier, V. Thouvenin, and G. Lefranc. IMGT unique numbering for immunoglobulin and T cell receptor constant domains and Ig superfamily C-like domains. Developmental and comparative immunology 29 (3), 2005.

Following these in silico selection steps, in vitro tests were carried out on the variants to determine protein yield (in vitro), aggregation/fragmentation, and binding kinetics.

Protein yield, as estimated by product titre in supernatant and after protein A purification must be at least 70% or higher of the parental molecule The percentage of monomer lost after conjugation measured through Size Exclusion Chromatography HPLC) is preferably ≤35%, more preferably ≤5%, ≤10%, ≤15%, ≤20%, ≤25%, or ≤30%.

Percentage aggregation of the conjugated molecule is preferably <5%, <10%, <15%, or <20%.

Percentage fragmentation of the conjugated antibody is preferably <5%, <10%, <15%, <20%, <25%, <30%, <32%, <35% or <40%.

The Constant of Dissociation (KD) of the conjugated variants must be equal to or less than 2 (≤2) orders of magnitude than the reference standard KD of an unmutated or parent antibody. For the antibodies described herein the reference standard is herceptin (trastuzumab), although it will be appreciated that where a different parent antibody is used, then that parent may be used as a reference standard.

Systems for cloning and expression of antibodies in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host for small immunoglobulin molecules is *E. coli*. The expression of immunoglobulins, such as antibodies and antibody fragments, in prokaryotic cells such as *E. coli* is well established in the art. Expression in eukaryotic cells in culture is also available to those skilled in the art as an option for production of a immunoglobulin. Immunoglobulins, such as antibodies and antibody fragments, may also be expressed in cell-free systems.

Suitable vectors for the expression of immunoglobulins can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992.

Nucleic acid encoding a variant immunoglobulin or a CH1, VH and/or VL domain thereof may be contained in a host cell.

Variant antibodies were generated as described for example in WO2011021009A1. In detail: DNA encoding the antibody variants as described herein were chemically synthesized and cloned into a suitable mammalian expression vector. For transient expression experiments heavy and light chain were cloned into separate expression vectors. For generation of cell lines stably expressing a variant antibody heavy and light chains were cloned into one single expression vector. Each expression vector comprises a DNA encoding a signal sequence upstream of the heavy chain and the light chain coding regions to enable secretion of the heavy and light chain from the mammalian cells.

For transient expression, CHOK1SV cells were transfected using for example Lipofectamine with the expression vectors encoding the variants as described herein.

For example in case of variants comprising at least one mutation in the light chain, an expression vector comprising said mutation(s) was co-transfected with a vector encoding the unmodified heavy chain; in case of variants comprising at least one mutation in the heavy chain, an expression vector comprising said mutation(s) was co-transfected with a vector encoding the unmodified light chain. 72 h post-transfection, supernatants were harvested form the transfected cells, centrifuged and stored at 4° C. prior to purification.

For Large scale production CHOK1SV cells are transfected as described above with a single vector comprising modified or unmodified light and heavy chain. Either pools of stably transfected cell are used for further experiments or a clonal selection is performed. Supernatants of such stable transfected cells expressing a variant of the present invention was harvested and stored at 4° C. prior to purification.

Cell culture supernatants were Protein A purified using HiTrap columns (GE) and stored at 4° C. prior to concentration and buffer exchange. Samples were concentrated by centrifugation at 2000 g 15-20 min. Material was buffer exchanged 4-5 times using formulation buffer (50 mM Phosphate, 100 mM NaCl, pH7.4). Once buffer exchanged, samples were diluted in formulation buffer to an appropriate working concentration.

Protein Yield Assessment (In Vitro)

The antibody or antibody variant yield is estimated by product titre in supernatant and after protein A purification (e.g. through sandwich ELISA, with absorbance at 280 nm, or via HPLC protein A quantification).

FIG. 1 shows levels of expression of each candidate antibody in 25 ml CHOK1SV cultures. All variants show similar levels of expression.

Conjugation

Conjugation was carried out with biotin-maleimide conjugation to free thiol groups by standard techniques Junutula J R et al, Nature Biotechnology 2008, 8, 925-932; Jeffrey S C et al, Bioconjugate Chem. 2013, 24, 1256-1263.

For conjugation to a toxin engineered antibodies are e.g. reduced with a tris(2-carboxyethyl)phosphine (12.5 eq.) for 2 h at 35° C. and pH 7.7. The mixture is buffer exchanged into 50 mM Tris, 5 mM EDTA, pH 7.7. Dehydroascorbic acid (15 eq.) is added and the oxidation reaction allowed to proceed for 3 h at 24° C. N,N-dimethylacetamide is added to reach a concentration of typically between 1 and 5%. Maleimidocaproyl-valine-citrulline-p-aminobenzyloxycarbonyl-monomethylauristatin E (5 eq.) is added and the conjugation reaction allowed to proceed for 1 h at 22° C. The reaction is quenched by addition of N-acetyl-cysteine (5 eq.). Following 0.5 h incubation at 22° C., the mixture is buffered exchanged into 1×PBS.

Aggregation Propensity/Fragmentation Assessment (In Vitro)

Before and after conjugation the percentage of monomer lost due to antibody aggregation and/or fragmentation was measured quantitatively using Size Exclusion Chromatography HPLC (SEC-HPLC) and qualitatively using SDS PAGE. For the latter, each variant antibody was treated with beta mercaptoethanol, or given no treatment, and size fractionated on a SDS PAGE. There was no apparent aggregation or fragmentation of the variants visible.

Results from SEC-HPLC analysis of conjugated and unconjugated samples are shown in FIG. 2, using samples at 1 mg/ml on a Zorbax-250GF column. Surprisingly some of the antibodies of the invention such as for example HC S139C, HC V170C, HC S160C, HC T200C, LC V191C, LC T2060, and LC T1800 showed less monomer lost, and/or decreased amount of antibody aggregation or fragmentation compared with the parent/unmutated antibody.

Binding Kinetics Assessment (In Vitro)

Binding kinetics of the variants were also analysed using a quartz crystal microbalance. ERB2/HER2 Fc chimaera were immobilized to carboxyl chip, and three different concentrations of each variant (conjugated and not conjugated) were tested. The table below summarises the Kd for each variant:

|  | $K_D$ (nM) | |
| --- | --- | --- |
| Reference | Not Conjugated | Conjugated |
| Herceptin | 3.0 | 1.63 |
| Variant | Not Conjugated | Conjugated |
| LCHerS208C | — | — |
| HCHerS443C | 4.36 | 31.13 |
| LCHerS202C | 12.22 | 0.72 |
| HCHerT200C | 3.52 | 12.91 |
| HCHerV170C | 3.43 | 2.90 |
| HCHerS447C | 3.17 | 1.34 |
| LCHerV191C | 4.94 | 3.56 |
| HCHerS445C | 1.27 | 1.74 |
| HCHerS168C | 18.11 | 1.55 |
| HCHerT190C | 1.26 | 2.28 |
| HCHerS139C | 3.56 | 2.44 |
| LCHerT206C | 9.41 | 19.91 |
| LCHerT180C | 5.19 | 1.46 |
| HCHerS160C | 9.76 | 1.50 |
| LCHerS182C | 5.28 | 0.008 |
| LCHerA184C | 1.25 | 1.04 |
| LCHerS203C | — | — |

Drug to Antibody Ratio (DAR) Assessment (In Vitro)

Finally, the DAR was determined for each of the variants, by liquid chromatography-electrospray ionization-tandem mass spectrometry (LC-ESI-MS/MS or LC-ESI-MS). The DAR values for the different variants must be >1.7 and <2.2, as there are two site specific conjugation sites per antibody.

For determining the DAR samples at 1 mg/ml were treated with PNGaseF. Reduced and not-reduced samples were analysed, by RP chromatography, electrospray, and mass spectrometry.

Figure 3:
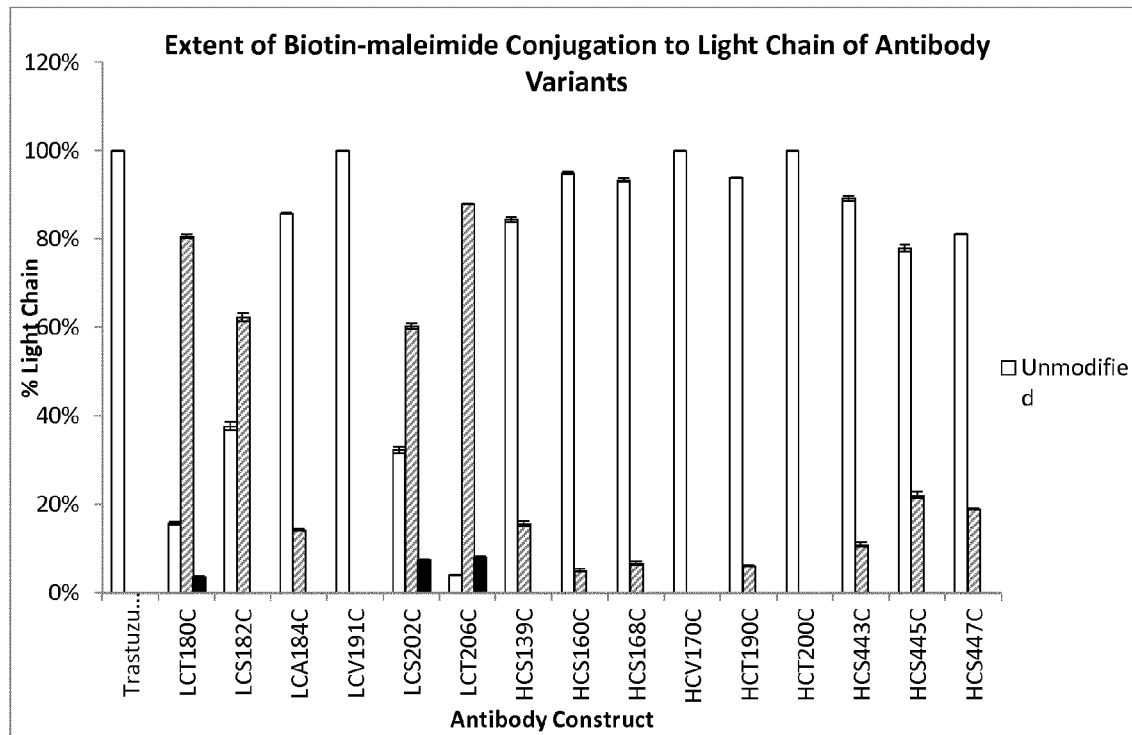
FIG. 3 shows extent of biotin-maleimide conjugation to light chains of antibody variants. Open bars represent unconjugated product, striped bars represent products with a single conjugated payload, and solid bars represent products with two conjugated payloads.
Figure 4:
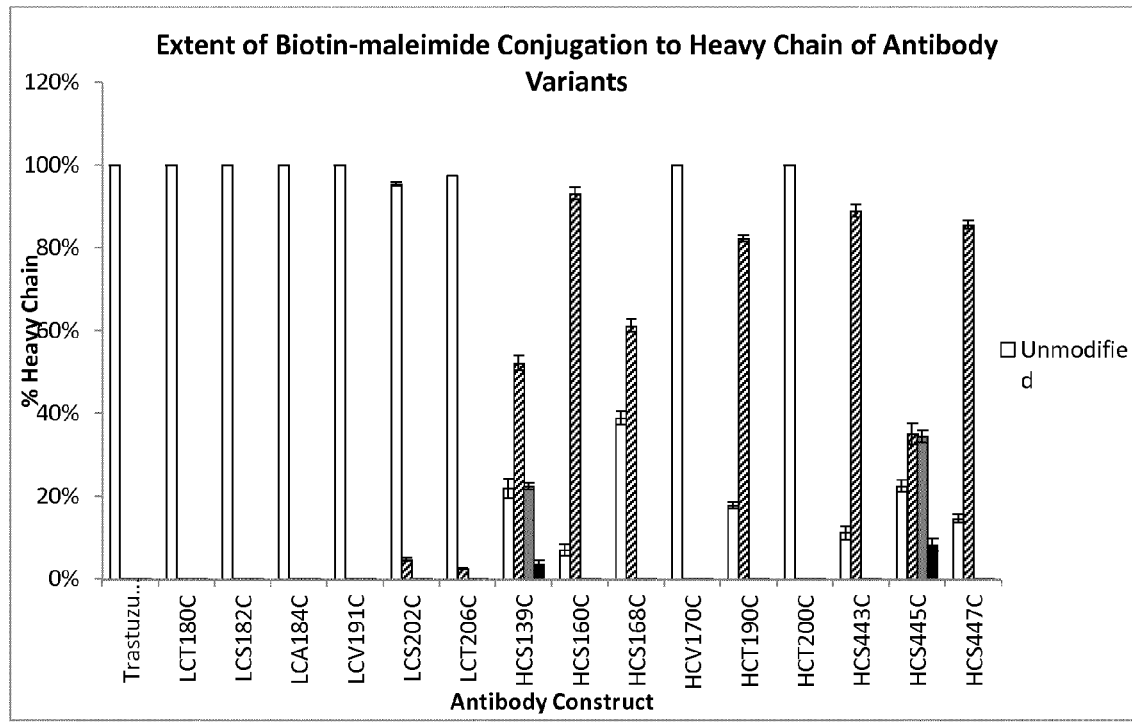
FIG. 4 shows extent of biotin-maleimide conjugation to heavy chains of antibody variants. Open bars represent unconjugated product, striped bars represent products with a single conjugated payload, and solid bars represent products with two conjugated payloads.
Figure 5:
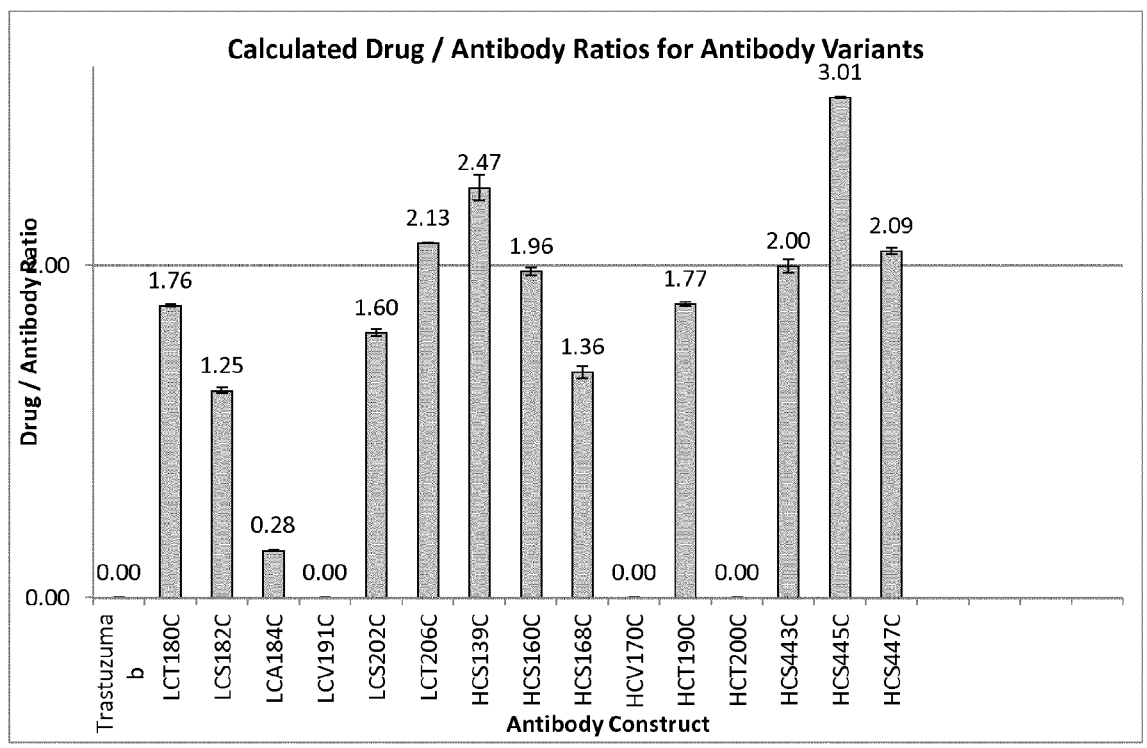
FIG. 5 shows calculated drug antibody ratio for the antibody variants of FIGS. 3 and 4.

The extent of biotin-maleimide conjugation to light and heavy chains of the variants is shown in FIGS. 3 and 4 respectively, with the calculated DAR for each variant being shown in FIG. 5.

Conjugation and De-Conjugation Assessment (In Vitro)

When stability of the ADC is analysed in vitro, the percentage average loss of conjugated molecule over a period of 8 days should be <39%.

Six preferred variants were selected, and each of the preferred six variants was then further analysed. Conjugate stability (levels of deconjugation) was determined for four different concentrations (150 ng/ml; 300 ng/ml; 1000 ng/ml and 2000 ng/ml) of each of the final variants in human serum at 37 deg C. for 8 days. Samples were taken on days 0, 2, 4, and 8, and analysed by ELISA.

The six final variants were: four heavy chain (S160C, T190C, S443C, S447C), and two light chain (T180C, or T206C) variants. As a result of the sequential method of selection all final variants can be expected to share a number of specific properties (or design criteria): Stability; low aggregation; low chemical degradation risk; low undesired post translational modifications; structural stability preserved; productivity; suitability for being conjugated; and biological activity.

The values for each tested variant are shown in the table below; the six final selected variants are highlighted.

|  | Prot A HPLC mg/L | SEC HPLC % Monomer conj, Ab | $K_D$ (nM) NOT CON-JUGATED | CON-JUGATED | LC MS Light Chain | | | LC MS Heavy Chain | | | | DAR |
|---|---|---|---|---|---|---|---|---|---|---|---|---|
|  |  |  |  |  | Un-modified | +1 Con-jugate | +2 Con-jugates | Un-modified | +1 Con-jugate | +2 Con-jugates | +3 Con-jugates |  |
| Herceptin | 55.13 | 78.53 | 3.02 | 1.63 | 100% | 0% | 0% | 100% | 0% | 0% | 0% | 0.00% |
| LCHerS208C | 48.11 | 54.06 | — | — | — | — | — | — | — | — | — | — |
| HCHerS443C | 54.96 | 60.83 | 4.36 | 31.13 | 89% | 11% | 0% | 11% | 89% | 0% | 0% | 2.00% |
| LCHerS202C | 55.00 | 69.00 | 12.22 | 0.72 | 32% | 60% | 7% | 95% | 5% | 0% | 0% | 1.60% |
| HCHerT200C | 58.83 | 94.94 | 3.52 | 12.91 | 100% | 0% | 0% | 100% | 0% | 0% | 0% | 0.00% |
| HCHerV170C | 55.42 | 93.54 | 3.43 | 2.90 | 100% | 0% | 0% | 100% | 0% | 0% | 0% | 0.00% |
| HCHerS447C | 49.11 | 66.94 | 3.17 | 1.34 | 81% | 19% | 0% | 15% | 85% | 0% | 0% | 2.09% |
| LCHerV191C | 56.37 | 95.73 | 4.94 | 3.56 | 100% | 0% | 0% | 100% | 0% | 0% | 0% | 0.00% |
| HCHerS445C | 57.93 | 77.22 | 1.27 | 1.74 | 78% | 22% | 0% | 22% | 35% | 34% | 8% | 3.01% |
| HCHerS168C | 57.68 | 78.01 | 18.11 | 1.55 | 93% | 7% | 0% | 39% | 61% | 0% | 0% | 1.36% |
| HCHerT190C | 46.22 | 77.19 | 1.26 | 2.28 | 94% | 6% | 0% | 18% | 82% | 0% | 0% | 1.77% |
| HCHerS139C | 60.58 | 80.27 | 3.56 | 2.44 | 84% | 16% | 0% | 22% | 52% | 22% | 4% | 2.47% |
| LCHerT206C | 53.83 | 82.70 | 9.41 | 19.91 | 4% | 88% | 8% | 97% | 3% | 0% | 0% | 2.13% |
| LCHerT180C | 46.87 | 84.58 | 5.19 | 1.46 | 16% | 81% | 4% | 100% | 0% | 0% | 0% | 1.76% |
| HCHerS160C | 55.47 | 81.03 | 9.76 | 1.50 | 95% | 5% | 0% | 7% | 93% | 0% | 0% | 1.96% |
| LCHerS182C | 51.18 | 73.15 | 5.28 | 8 × 10 − 3 | 38% | 62% | 0% | 100% | 0% | 0% | 0% | 1.25% |
| LCHerA184C | 60.11 | 80.20 | 1.25 | 1.04 | 86% | 14% | 0% | 100% | 0% | 0% | 0% | 0.28% |
| LCHerS203C | 53.61 | 58.22 | — | — | — | — | — | — | — | — | — | — |

Figure 6:
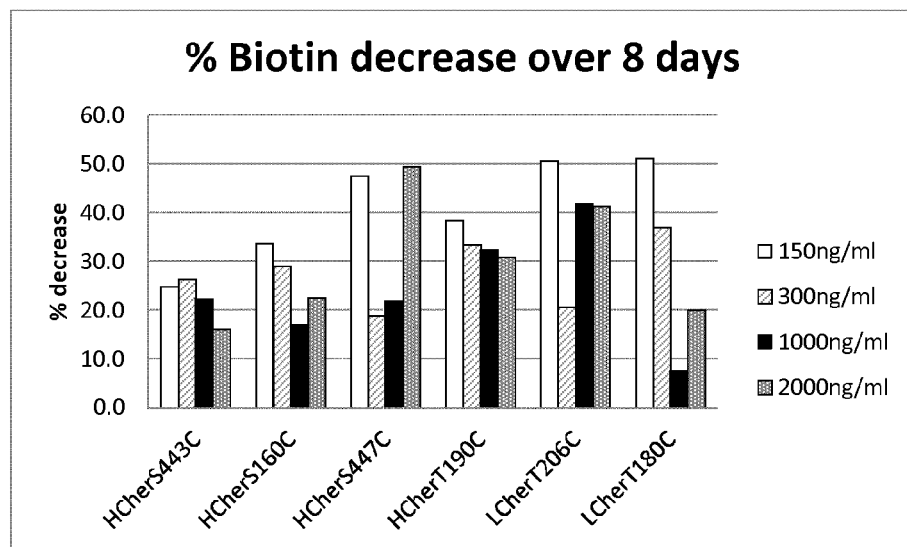
FIG. 6 shows percentage biotin decrease over time for the subset of antibody variants.
Figure 6:
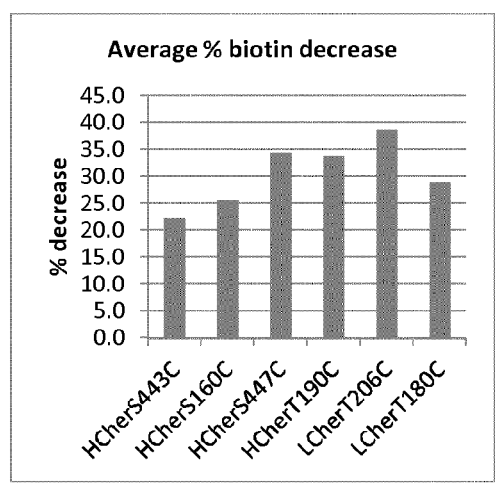

The percentage biotin decrease over 8 days is shown in FIG. 6.

Each of the final six variants was then ranked for desirable characteristics (purity, DAR, deconjugation, and positive environment), and given a score from 6 (=best) to 1 (=worst). The scores were then totaled, to give an overall score from 4 to 24. This gives an indication of the desirability of each antibody for further development. The scores are shown in the table below.

|  | Purity | | DAR | | % Deconjugation | | Positive Environment | | Total |
|---|---|---|---|---|---|---|---|---|---|
| HCHerS443C | 60.83 | 1 | 2.00 | 6 | 29 | 6 | LYS | 6 | 19 |
| HCHerS447C | 66.94 | 2 | 2.09 | 4 | 40 | 1 |  | 2 | 9 |
| HCHerT190C | 77.19 | 3 | 1.77 | 2 | 37 | 3 |  | 2 | 10 |
| LCHerT206C | 82.7 | 5 | 2.13 | 3 | 40 | 1 | LYS | 6 | 15 |
| LCHerT180C | 84.58 | 6 | 1.76 | 1 | 32 | 5 |  | 2 | 14 |
| HCHerS160C | 81.03 | 4 | 1.96 | 5 | 32 | 5 |  | 2 | 16 |

Although the antibody variants can be ranked in this way, as each of the final six has been through the initial selection process, they can all be said to have desirable characteristics for development as an ADC. In particular, not every antibody will make it through subsequent drug development processes and in vivo testing, so it is beneficial to be able to generate a selection of candidates. Furthermore, other variants not selected for the final six, such as the remaining variants disclosed herein, may also have beneficial properties and so may be considered useful for further investigation.

Figure 7:
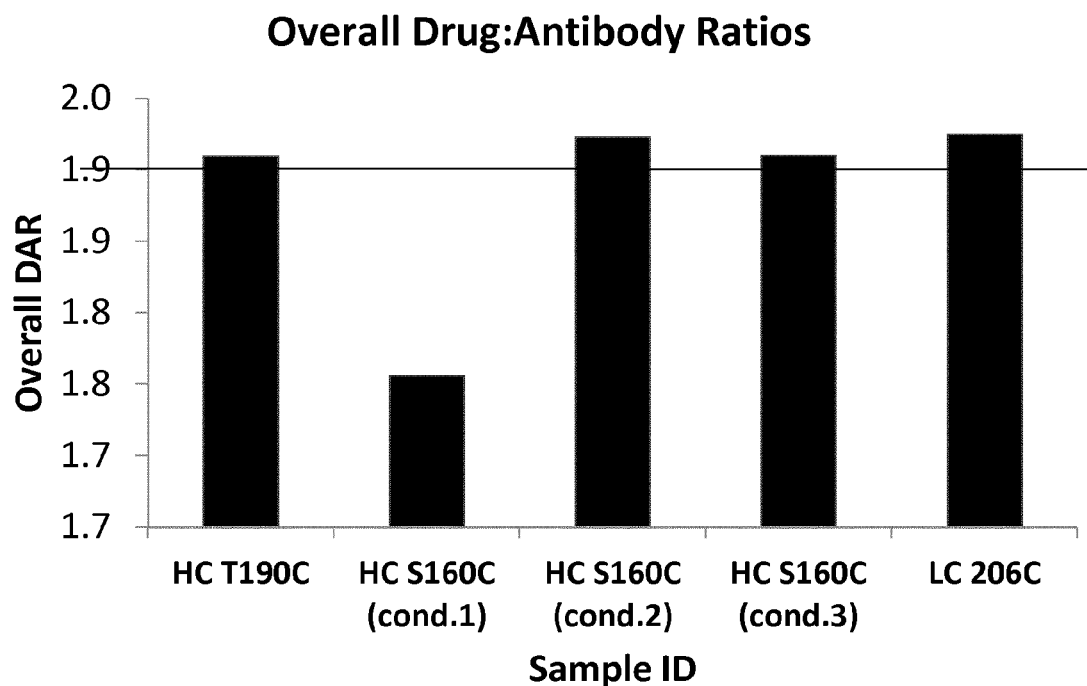
FIG. 7 shows calculated drug to antibody ratio of some of the selected variants conjugated to MMAE.

Subsequently the final six variants were conjugated to Monomethyl Auristatin E (MMAE) by standard techniques. The conjugation method follows broadly methods described above. The DAR for the selected variants was determined as described above. An example of the results is shown in FIG. 7. Cond 1-3 represent minor variants in the conjugation procedure with parameters varied to try to optimise the DAR; the reduction time and temperature for antibodies prior to conjugation were varied in each of conditions 1-3:

Condition 1: reduction at 35° C. for 2 h (as described above)

Condition 2: reduction at 25° C. for 2 h

Condition 3: reduction at 35° C. for 1 h.

A double mutant (DM) combining LC T180C and HC S160C was also tested to determine aggregation propensity and DAR data, using the same techniques as described above. The results are shown in the following tables:

DM Aggregation Data from the Transient Transfections using size-exclusion chromatography SEC

|  | Relative % by SEC | |
|---|---|---|
| Species | Before conjugation | After conjugation |
| Purity, main peak | 95.4 | 96.1 |
| High molecular weight forms | 3.0 | 3.0 |
| Low molecular weight forms | 1.6 | 0.9 |

DM DAR Data from the Transient Transfections using PLRP HPLC or ESI-MS methods

| Variant | PLRP | Intact mass |
|---------|------|-------------|
| DM      | 3.77 | 3.97        |

In Vitro Toxicity Tests

After MMAE conjugation the ADC variants were tested for in vitro cytotoxicity. The analysis was carried out by standard techniques (Andreotti, P. E. et al. Cancer Res 1995.55, 5276-82; Gerhardt, R. T. et al. Am. J. Obstet. Gynecol 1991 165, 245-55). The cells chosen for the assay were based on Neve R. M. et al. Cancer Cell 2006 10, 515-527.

Assay Schematics:

Day 1: Seed three 96-well plates each of SKBR3 cells (5 k/well) in media (McCoy5A+10% FBS+1×Pen/Strep), BT474 cells (8 k/well) in media (DMEM/F12+10% FBS+1×Pen/Strep), and MCF7 cells (4 k/well) in media (RPMI+10% FBS+1×Pen/Strep). Incubate in 37° C. humidified CO2 incubator for 18 hrs.

Day 2: Prepare ADC variants sample dilutions. Make the initial 667 nM working stocks of these samples in RPMI media with 10% FBS. Then prepare ⅓ serial dilution from 667 nM to 11 pM in media. Add 5 ul of the dilution into each well of ~100 ul cells. Final sample concentrations range from 33.3 nM to 0.56 pM (as ⅓ serial dilutions). Incubate at 37° C. in a humidified CO2 incubator for 72 hrs.

Day 4: Evaluate the plates under a microscope

Day 5: Determine cell viability using Cell-Titer Glo reagent:

Aspirate the media from the 96-well plate.
Add 100 ul of Cell-Titer Glo reagent (Promega Inc.) in each well. Incubate at room temperature for 10 min.
Determine luminescence using Tecan Ultra plate reader.
Analyze and plot data either as Percent Viability vs. Concentration (nM), or as random luminesce.

Figure 8:
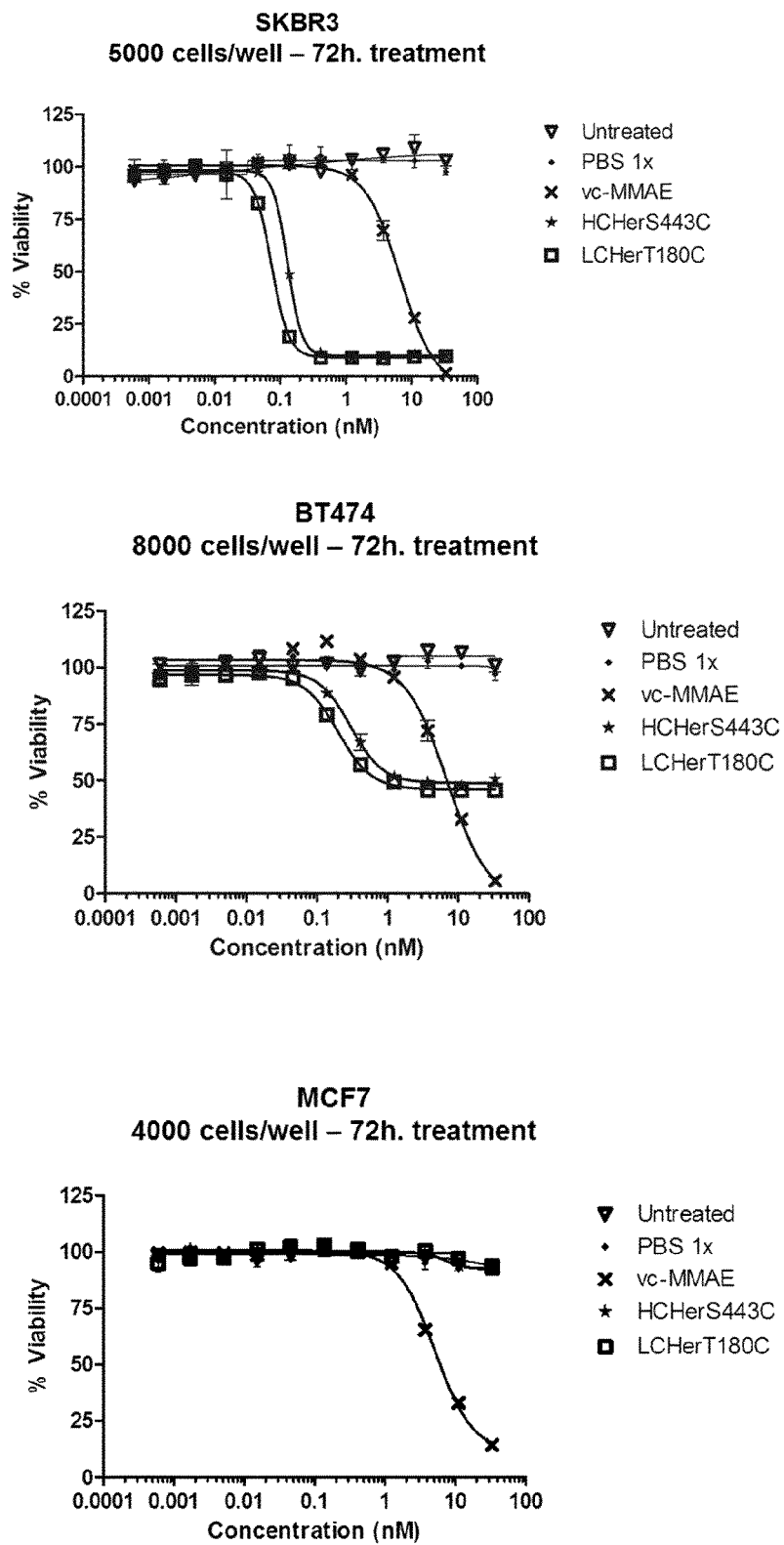
FIG. 8 shows the decrease in cell viability for different cell lines that have been exposed to different concentrations of the selected ADC over a period of 72 h. PBS=phosphate buffered saline; vc-MMAE=valine-citrulline-MMAE.

An example of the results is shown in FIG. 8. As can be seen in FIG. 8, ADC variants HC S443C and LC T180C reduce the viability of SKBR3 cells and BT474 cells by 50% at very low concentrations, whereas these ADC variants do not show an effect over 72 hours in less responsive cells like MCF7.

The full sequences of the variant chain of each of the variants described herein are shown below. These show only the variant chain; the other chain will be the same as the unmodified trastuzumab sequence (that is, SEQ ID No 1 (LC) or 2 (HC)).

```
Heavy chains:
>HCherS139C
                                       (SEQ ID No 3)
EVQLVESGGGLVQPGGSLRLSCAASGENIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTCGGTAA

LGCLVKDYFPEPVTVSWNSGALTSGVHTFPAVLQSSGLYSLSSVVTVP

SSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMH

EALHNHYTQKSLSLSPGK

>HCherS160C
                                       (SEQ ID No 4)
EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTAA

LGCLVKDYFPEPVTVCWNSGALTSGVHTFPAVLQSSGLYSLSSVVTVP

SSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMH

EALHNHYTQKSLSLSPGK

>HCherS168C
                                       (SEQ ID No 5)
EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTAA

LGCLVKDYFPEPVTVSWNSGALTCGVHTFPAVLQSSGLYSLSSVVTVP

SSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMH

EALHNHYTQKSLSLSPGK

>HCherV170C
                                       (SEQ ID No 6)
EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTAA

LGCLVKDYFPEPVTVSWNSGALTSGCHTFPAVLQSSGLYSLSSVVTVP

SSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEW

ESNGQPENNYKTTPPVLDSDGSFFLYSKLTVDKSRWQQGNVESCSVMH

EALHNHYTQKSLSLSPGK

>HCherV176C
                                       (SEQ ID No 7)
EVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYC

SRWGGDGFYAMDYWGQGTLVTVSSASTKGPSVFPLAPSSKSTSGGTAA
```

```
LGCLVKDYFPEPVTVSWNSGALTSGVHTFPACLQSSGLYSLSSVVTVP
SSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMH
EALHNHYTQKSLSLSPGK

>HCherT190C                                    (SEQ ID No 8)
EVQLVESGGGLVQPGGSLRLSCAASGFNIKDTYIHWVRQAPGKGLEWV
ARIYPTNGYTRYADSVKGRFTISADTSKNTAYLQMNSLRAEDTAVYYC
SRWGGDGFYAMDYWGQGTLVTVSSASTKGPSVFPLAPSSKSTSGGTAA
LGCLVKDYFPEPVTVSWNSGALTSGVHTFPAVLQSSGLYSLSSVVCVP
SSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMH
EALHNHYTQKSLSLSPGK >HCherT200C                                    (SEQ ID No 9)
EVQLVESGGGLVQPGGSLRLSCAASGFNIKDTYIHWVRQAPGKGLEWV
ARIYPTNGYTRYADSVKGRFTISADTSKNTAYLQMNSLRAEDTAVYYC
SRWGGDGFYAMDYWGQGTLVTVSSASTKGPSVFPLAPSSKSTSGGTAA
LGCLVKDYFPEPVTVSWNSGALTSGVHTFPAVLQSSGLYSLSSVVTVP
SSSLGTQCYICNVNHKPSNTKVDKRVEPKSCDKTHTCPPCPAPELLGG
PSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMH
EALHNHYTQKSLSLSPGK >HCherS443C                                    (SEQ ID No 10)
EVQLVESGGGLVQPGGSLRLSCAASGFNIKDTYIHWVRQAPGKGLEWV
ARIYPTNGYTRYADSVKGRFTISADTSKNTAYLQMNSLRAEDTAVYYC
SRWGGDGFYAMDYWGQGTLVTVSSASTKGPSVFPLAPSSKSTSGGTAA
LGCLVKDYFPEPVTVSWNSGALTSGVHTFPAVLQSSGLYSLSSVVTVP
SSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMH
EALHNHYTQKCLSLSPGK >HCherS445C                                    (SEQ ID No 11)
EVQLVESGGGLVQPGGSLRLSCAASGFNIKDTYIHWVRQAPGKGLEWV
ARIYPTNGYTRYADSVKGRFTISADTSKNTAYLQMNSLRAEDTAVYYC
SRWGGDGFYAMDYWGQGTLVTVSSASTKGPSVFPLAPSSKSTSGGTAA
LGCLVKDYFPEPVTVSWNSGALTSGVHTFPAVLQSSGLYSLSSVVTVP
SSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMH
EALHNHYTQKSLCLSPGK >HCherS447C                                    (SEQ ID No 12)
EVQLVESGGGLVQPGGSLRLSCAASGFNIKDTYIHWVRQAPGKGLEWV
ARIYPTNGYTRYADSVKGRFTISADTSKNTAYLQMNSLRAEDTAVYYC
SRWGGDGFYAMDYWGQGTLVTVSSASTKGPSVFPLAPSSKSTSGGTAA
LGCLVKDYFPEPVTVSWNSGALTSGVHTFPAVLQSSGLYSLSSVVTVP
SSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMH
EALHNHYTQKSLSLCPGK Light chains:
>LCherS171C                                    (SEQ ID No 13)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TFGQGTKVEIKRTVAAPSVFIFPPSDEQLKSGTASVVCLLNNFYPREA
KVQWKVDNALQSGNSQESVTEQDSKDCTYSLSSTLTLSKADYEKHKVY
ACEVTHQGLSSPVTKSFNRGEC >LCherT180C                                    (SEQ ID No 14)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TFGQGTKVEIKRTVAAPSVFIFPPSDEQLKSGTASVVCLLNNFYPREA
KVQWKVDNALQSGNSQESVTEQDSKDSTYSLSSTLCLSKADYEKHKVY
ACEVTHQGLSSPVTKSFNRGEC >LCherS182C                                    (SEQ ID No 15)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TEGQGTKVEIKRTVAAPSVFIFPPSDEQLKSGTASVVCLLNNFYPREA
KVQWKVDNALQSGNSQESVTEQDSKDSTYSLSSTLTLCKADYEKEKVY
ACEVTHQGLSSPVTKSFNRGEC
```

>LCherA184C
(SEQ ID No 16)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TFGQGTKVEIKRTVAAPSVFIFPPSDEQLKSGTASVVCLLNNFYPREA
KVQWKVDNALQSGNSQESVTEQDSKDSTYSLSSTLTLSKCDYEKHKVY
ACEVTHQGLSSPVTKSFNRGEC >LCherV191C
(SEQ ID No 17)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKCY
ACEVTHQGLSSPVTKSFNRGEC >LCherS202C
(SEQ ID No 18)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLCSPVTKSFNRGEC >LCherS203C
(SEQ ID No 19)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSCPVTKSFNRGEC >LCherT206C
(SEQ ID No 20)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVCKSFNRGEC >LCherS208C
(SEQ ID No 21)
DIQMTQSPSSLSASVGDRVTITCRASQDVNTAVAWYQQKPGKAPKLLI
YSASFLYSGVPSRFSGSRSGTDFTLTISSLQPEDFATYYCQQHYTTPP
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKCFNRGEC It will be appreciated that a similar selection and screening process may be used to develop other variant antibodies, not only those based on trastuzumab, and further that it may be expected that variants of these other antibodies having the same constant region mutations as identified herein would also be expected to have similar desirable properties.

The invention claimed is:

1. An antibody, or a fragment or derivative thereof, having a variable region which binds a target molecule, and a constant region, wherein the constant region comprises one or more mutations introducing a site specific conjugation site selected so as to permit conjugation of the antibody, fragment, or derivative to a payload, wherein the antibody comprises the amino acid sequence of SEQ ID NO: 36; where X is selected from C, K, or Q.

2. The antibody of claim 1, wherein the antibody is selected from the group comprising IgG1, IgG2, IgG3, and IgG4.

3. The antibody of claim 2, wherein the constant region comprises one or more of the Ck, CH1 and CH3 domains of the IgG1 constant region.

4. The antibody of claim 1, wherein the antibody is selected from the group consisting of Fabs, bi specific antibody fragments (tandem scFv-Fc, scFv-Fc knobs-into-holes, scFv-Fc-scFv, F(ab')2, Fab-scFv, (Fab'scFv)2, scDiabody-Fc, or scDiabody-CH3), IgG-based bispecific antibodies (Hybrid hybridoma, Knobs-into-holes with common light chain, Two-in-one IgG, Dual V domain IgG, IgG-scFv, scFv-IgG, IgG-V, V-IgG), minibody, tribi-minibody, nanobodies, and di-diabody.

5. The antibody of claim 1, wherein the antibody is selected from Abciximab; Rituximab; Basiliximab; Daclizumab; Palivizumab; Infliximab; Trastuzumab; Alemtuzumab; Adalimumab; Efalizumab; Cetuximab; Ibritumomab; Omalizumab; Bevacizumab; Ranibizumab; Golimumab; Canakinumab; Ustekinumab; Tocilizumab; Ofatumumab; Belimumab; Ipilimumab; Brentuximab; Pertuzumab; Raxibacumab; Vedolizumab; Ramucirumab; Obinutuzumab; Siltuximab; Secukinumab; Dinutuximab.

6. The antibody of claim 1, which lacks one or more Fc effector functions.

7. An immunoconjugate comprising the antibody of claim 1, a payload, and a linker joining the payload to the antibody.

8. The immunoconjugate of claim 7, wherein the linker is selected from 6-maleimidocaproyl (MC), maleimidopropanoyl (MP), valine-citrulline (val-cit), alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1 carboxylate (SMCC), N-Succinimidyl, (4-iodo-acetyl) aminobenzoate (SIAB),), SPDB, hydrazone, maleimidocaproyl and 6-maleimidocaproyl-valine-citrulline-p-aminobenyloxycarbonyl (MC-vc-PAB); or is a branched linker which comprises a peptide chain and is derived from o-hydroxy p-amino benzylic alcohol, wherein the peptide chain is connected to the phenyl ring via the p-amino group, the payload is connected to the phenyl ring via the benzylic alcohol moiety, and the antibody is connected to the phenyl ring via the o-hydroxy group.

9. The immunoconjugate of claim 7, wherein the payload is selected from the group consisting of 90Y, 131I, 67Cu, 177Lu, 213Bi, 211At, dolastatin, vedotin, monomethyl auristatin F(MMAF), monomethyl auristatin E (MMAE); maytansinoids including DM1 and DM4, duocarmycin, duocarmycin analogs, calicheamicin, pyrrolobenzodiazepines (PBD), centanamycin, irinotecan, and doxorubicin, alphaamanitin, melatonin, membrane disrupting peptide, *Pseudomonas* exotoxin A, Diphtheria toxin, ricin, polyethylene glycol, hydroxyethyl starch, and a mannosyl residue.

10. A pharmaceutical composition comprising an antibody according to claim 1, and a pharmaceutically acceptable diluent, carrier or excipient.

11. A method for generating an immunoconjugate, the method comprising conjugating the antibody of claim 1 to a payload.

12. An isolated or recombinant polynucleotide encoding the antibody of claim 1.

13. A vector comprising the polynucleotide of claim 12.

14. A host cell comprising the vector of claim 13.

15. A method of producing an antibody comprising:
    (a) providing a culture medium comprising the host cell of claim 14; and
    (b) placing the culture medium in conditions under which the antibody is expressed, and optionally
    (c) isolating the antibody.

16. The antibody of claim 1, further comprising a mutation at one or more of heavy chain positions 160, 190, 168, 170, 176 or 200.

17. The antibody of claim 1, wherein the light chain is a kappa light chain.

* * * * *